(12) United States Patent
Nakagawa et al.

(10) Patent No.: US 6,825,181 B1
(45) Date of Patent: Nov. 30, 2004

(54) AMINOISOQUINOLINE DERIVATIVES

(75) Inventors: Tadakiyo Nakagawa, Kawasaki (JP); Shingo Makino, Kawasaki (JP); Kazuyuki Sagi, Kawasaki (JP); Masaru Takayanagi, Kawasaki (JP); Takashi Kayahara, Kawasaki (JP); Shunji Takehana, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 407 days.

(21) Appl. No.: 09/665,633

(22) Filed: Sep. 19, 2000

Related U.S. Application Data

(63) Continuation of application No. PCT/JP99/01309, filed on Mar. 17, 1999.

(30) Foreign Application Priority Data

Mar. 19, 1998 (JP) .............................................. 10/070771
Jul. 13, 1998 (JP) .............................................. 10/197133

(51) Int. Cl.$^7$ ..................... A61K 31/66; A61K 31/47; A61K 31/655; C07F 9/28; C07D 453/02
(52) U.S. Cl. ..................... 514/146; 514/310; 514/149; 546/23; 546/135
(58) Field of Search ............................... 514/310, 146, 514/149; 546/135, 23

(56) References Cited

U.S. PATENT DOCUMENTS 3,847,919 A * 11/1974 Knowles et al.
6,262,069 B1   7/2001 Liebeschuetz et al.

FOREIGN PATENT DOCUMENTS

| JP | 61-172861 | 8/1986 |
| JP | 6-80569 | 3/1994 |
| WO | WO 98/25611 | 6/1998 |
| WO | WO 98/31661 | 7/1998 |
| WO | WO 98/47876 | 10/1998 |
| WO | WO 99/11657 | 3/1999 |
| WO | WO 99/47503 | 9/1999 |
| WO | WO 99/62904 | 12/1999 |
| WO | WO 00/71493 A2 | 11/2000 |
| WO | WO 00/71507 A2 | 11/2000 |
| WO | WO 00/71508 A2 | 11/2000 |
| WO | WO 00/71509 A1 | 11/2000 |
| WO | WO 00/71510 A2 | 11/2000 |
| WO | WO 00/71511 A2 | 11/2000 |
| WO | WO 00/71512 A1 | 11/2000 |
| WO | WO 0071515 A2 | 11/2000 |
| WO | WO 0071516 A2 | 11/2002 |

OTHER PUBLICATIONS

Wiley, et al., *J. Med. Chem.*, vol. 43, pp. 883–899 (2000).
Pinto, et al., *J. Med. Chem.*, vol. 44, pp. 566–578 (2001).
Xu, et al., *Synthesis*, vol. 7, pp. 556–558 (1983).
Saulnier, et al., *J. Am. Chem. Soc.*, vol. 111, pp. 8320–8321 (1989).

*Thrombosis and Haemostasis*, vol 74(2), pp. 635–639, 1995.

*Thrombosis Research*, vol. 83, pp. 117–126, 1996.

*European Journal of Pharmacology*, vol. 352, pp. 59–63, 1998.

*Journal of Medicinal Chemistry*, vol. 43, pp. 4398–4415, 2000.

*Journal of Medicinal Chemistry*, vol. 43, pp. 883–899, 2000.

*Journal of Medicinal Chemistry*, vol. 44, pp. 566–578, 2001.

R.R. Tidwell, et al., "Strategies for Anticoagulation with Synthetic Protease Inhibitors, Xa Inhibitors versus Thrombin Inhibitors", Thrombosis Research, vol. 19, pp. 339–349, 1980.

(List continued on next page.)

*Primary Examiner*—Alan L. Rotman
*Assistant Examiner*—Binta Robinson
(74) *Attorney, Agent, or Firm*—Oblon, Spivak, McClelland, Maier & Neustadt, P.C.

(57) ABSTRACT

Aminoisoquinoline derivatives of the following formulae or analogs thereof and pharmaceutically acceptable salts thereof are provided. These compounds have an excellent effect of inhibiting activated blood-coagulation factor X, and they are useful as anticoagulants or agents for preventing or treating thrombi or emboli.

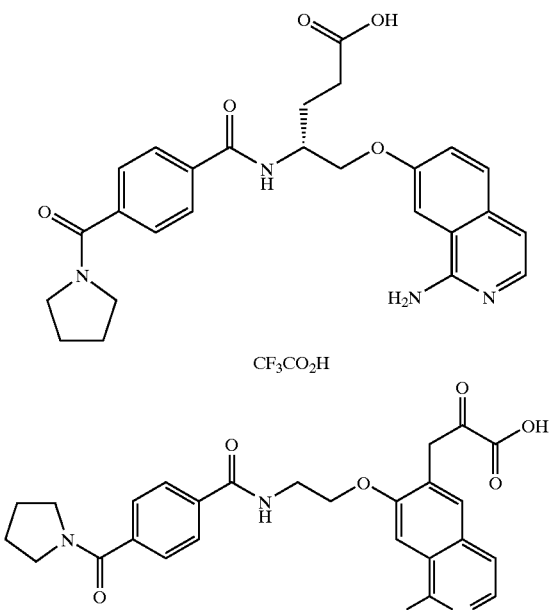

15 Claims, No Drawings

OTHER PUBLICATIONS

David J. Robison, et al., "Active Site of Bovine Factor Xa, Characterization using Substituted Benzamidines as Competitive Inhibitors and Affinity–Labeling Reagents", The Journal Of Biological Chemistry, vol. 255, No. 5, Issue of Mar. 10, pp. 2014–2021, 1980.

Wong, et al., *Thrombosis Research*, vol. 83, No. 2, pp. 117–126 (1996).

Han, et al., *J. Med. Chem.*, vol. 43, pp. 4398–4415 (2000).

Drake NL, in *Organic Reactions*, vol. 1, Chapter 5, pp. 105–128, Wiley, NY, 1942.

* cited by examiner

AMINOISOQUINOLINE DERIVATIVES

This application is a continuation of PCT/JP99/01309, filed Mar. 17, 1999.

BACKGROUND OF THE INVENTION

The present invention relates to new aminoisoquinoline derivatives which can be orally administrated to exhibit a strong anticoagulant effect by inhibiting activated blood-coagulation factor X; anticoagulants containing them as active ingredients; and agents for preventing or treating diseases caused by thrombi or emboli. These diseases include, for example, cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; generalized intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

As the habit of life is being westernized and people of advanced ages are increasing in Japan, thrombotic and embolismic patients such as those suffering from myocardial infarction, cerebral thrombosis and peripheral thrombosis are increasing in number year by year, and the treatment of patients with these diseases is becoming more and more important in the society. Anticoagulation treatment is included in the internal treatments for the remedy and prevention of thrombosis, like radiotherapy and antithrombocytic therapy.

Antithrombins were developed as thrombus-formation inhibitors in the prior art. However, it has been known that since thrombin not only controls the activation of fibrinogen to form fibrin, which is the last step of the coagulation reaction, but also deeply relates to the activation and coagulation of blood platelets, the inhibition of the action of thrombin causes a danger of causing hemorrhage. In addition, when antithrombins are orally administered, the bioavailability thereof is low. At present, no antithrombin which can be orally administered is available on the market.

Since the activated blood coagulation factor X is positioned at the juncture of an exogenous coagulation cascade reaction and an endogenous coagulation cascade reaction and in the upstream of thrombin, it is possible to inhibit the coagulation system more efficiently and specifically, than the thrombin inhibition, by inhibiting the factor X (THROMBOSIS RESEARCH, Vol. 19, pages 339 to 349; 1980).

DISCLOSURE OF THE INVENTION

The object of the present invention is to provide compounds having an excellent effect of inhibiting the effect of activated blood coagulation factor X.

Another object of the present invention is to provide compounds having an effect of specifically inhibiting the effect of activated blood coagulation factor X, which can be orally administered.

Still another object of the present invention is to provide a blood-coagulation inhibitor or an agent for preventing or treating thrombosis of embolism, which contains one of the above-described compounds.

After intensive investigations made under these circumstances, the inventors have found that specified new aminoisoquinoline derivatives have an excellent effect of inhibiting activated blood coagulation factor X and are usable for preventing and treating various diseases caused by thrombi and emboli. The present invention has been completed on the basis of this finding.

Namely, the present invention provides aminoisoquinoline derivatives of following general formula (1) or pharmaceutically acceptable salts thereof:

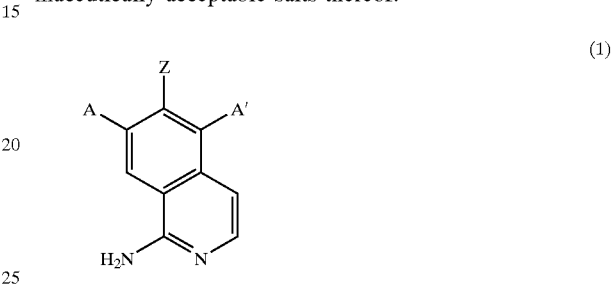
(1)

In general formula (1), A represents an organic group of following formula (2) and A' represents a hydrogen atom, or A' represents an organic group of following formula (2) and A represents a hydrogen atom:

$$V-L-Y- \quad (2)$$

In formula (2), L represents an organic group of any of the following formulae (3) to (6):

(3)

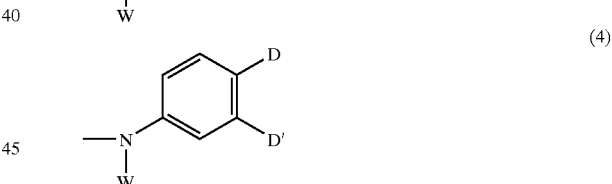
(4)

$$-CH_2CH_2- \quad (5)$$

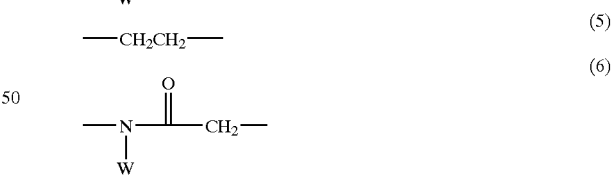
(6)

In above formulae (3), (4) and (6), W represents a hydrogen atom, an alkyl group having 1 to 6 carbon atoms, an aryl group having 4 to 10 carbon atoms, an aralkyl group having 5 to 12 carbon atoms or a carboxyalkylsulfonyl group having 2 to 4 carbon atoms.

W is, for example, hydrogen atom, methyl group or benzyl group.

One of D and D' in formula (4) represents a bond to Y in general formula (2) and the other represents a hydrogen atom.

In formula (3), X represents a hydrogen atom, a carboxyl group, an alkoxycarbonyl group having 1 to 3 carbon atoms, an alkyl group having 1 to 3 carbon atoms which may have a substituent or a benzyl group which may have a substituent. The substituent is selected from among carboxyl group, alkoxycarbonyl groups having 2 to 10 carbon atoms, alkylsulfonyloxy groups having 1 to 6 carbon atoms, piperidyloxy group, iminoalkylpiperidyloxy groups having 6 to 10 carbon atoms, alkoxycarbonylpiperidyloxy groups having 7 to 14 carbon atoms, piperidylalkyl groups having 6 to 8 carbon atoms, iminoalkylpiperidylalkyl groups having 7 to 11 carbon atoms, alkoxycarbonylpiperidylalkyl groups having 8 to 15 carbon atoms, pyrrolidyloxy group, iminoalkylpyrrolidyloxy groups having 5 to 9 carbon atoms, alkoxycarbonylpyrrolidyloxy groups having 7 to 13 carbon atoms, amidino group, mono- or dialkylamidino groups having 2 to 7 carbon atoms, hydroxyl group, halogeno groups, indolyl group and alkyl groups having 1 to 5 carbon atoms.

In formula (3), X and W may be bonded together to form a ring and, in this case, —W—X— represents an ethylene group, trimethylene group or tetramethylene group.

When L is an organic group of any of formulae (3) to (5), V represents a hydrogen atom, an alkanesulfonyl group having 1 to 6 carbon atoms, which may have a substituent, or a benzoyl, benzenesulfonyl, 2-naphthalenesulfonyl, cinnamoyl, piperidinecarbonyl, phenylacetyl, pyridinecarbonyl, thiophenecarbonyl, phenylthiocarbonyl or benzimidoyl group which may have a substituent. When L is an organic group of formula (6), V represents an aryl group having 4 to 10 carbon atoms, which may have a substituent.

When L is an organic group of any of formulae (3) to (6) and V has a substituent, the substituent is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, trialkylamidino groups having 4 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylamino groups having 2 to 7 carbon atoms, N-alkyl-N-alkoxycarbonylaminoalkyl groups having 4 to 10 carbon atoms, piperidyloxy group, acylpiperidyloxy groups having 6 to 9 carbon toms, iminoalkylpiperidyloxy groups having 6 to 10 carbon atoms, alkoxycarbonylpiperidyloxy groups having 8 to 14 carbon atoms, pyrrolidyloxy group, iminoalkylpyrrolidyloxy groups having 5 to 9 carbon atoms, alkoxycarbonylpyrrolidyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperididenealkyl groups having 6 to 9 carbon atoms, iminoalkylpiperidinealkyl groups having 8 to 12 carbon atoms, guanidino group, phosphono group, dialkoxyphosphoryl groups having 2 to 9 carbon atoms, monoalkoxyhydroxyphosphoryl groups having 1 to 4 carbon atoms and dialkylguadinino groups having 3 to 5 carbon atoms.

In formula (2), Y represents a group of any of the following formulae (7) to (13):

(7)

(8)

(9)

(10)

(11)

(12)

(13)

In formulae (7) and (8), n represents an integer of 1 or 2. In formula (13), $R^1$ represents a hydrogen atom, a hydroxycarbonylalkyl group having 2 to 7 carbon atoms, an alkoxycarbonylalkyl group having 3 to 8 carbon atoms or a hydroxycarbonylalkenyl group having 3 to 7 carbon atoms.

Z represents a hydrogen atom, an alkyl group having 1 to 6 carbon atoms, a halogeno group, an amino group or a group of any of following formulae (14) to (19):

(14)

(15)

(16)

(17)

(18)

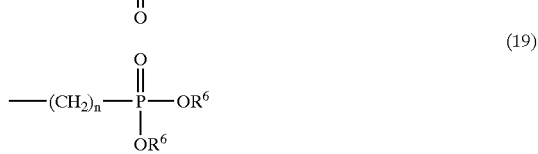
(19)

in formulae (14) and (17) to (19), n represents an integer of 0 to 3. In formula (14), $R^2$ represents a hydroxyl group, a carboxyl group, an amino group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms. In formula (15), $R^3$ represents a carboxyl group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms; $R^4$ represents a hydrogen atom, an alkoxycarbonylamino group having 2 to 7 carbon atoms or an alkylcarbonylamino group having 2 to 7 carbon atoms. In formula (16), $R^5$ represents a hydroxyl group, an amino group, an aryl group having 4 to 10 carbon atoms, an alkoxyl group having 1 to 3 carbon atoms or an aralkyl group having 5 to 12 carbon atoms. In formulae (17) to (19), $R^6$ represents a hydrogen atom or an alkyl group having 1 to 6 carbon atoms.

The present invention also relates to aminoisoquinoline derivatives of following general formula (20), which have an effect of inhibiting the effect of activated blood coagulation factor X, and pharmaceutically acceptable salts of them.

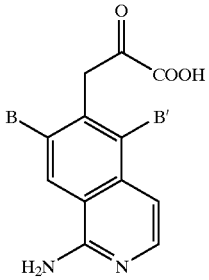

(20)

wherein one of B and B' represents an oil-soluble organic group and the other represents a hydrogen atom.

The present invention also provides a medicinal composition containing any of the above-described aminoisoquinoline derivatives and salts thereof as the active ingredient.

Further, the present invention provides an anticoagulant containing any of the above-described aminoisoquinoline derivatives and salts thereof as the active ingredient, or an agent for preventing or treating thrombi or emboli.

BEST MODE FOR CARRYING OUT THE INVENTION

The alkyl groups in the present invention may be branched or have a ring. For example, the alkyl groups include cyclohexylmethyl group or the like. The term "aryl" herein involves not only aromatic cyclic hydrocarbon groups but also aromatic heterocyclic groups having 1 to 3 heteroatoms selected from among O, N and S. Examples of the aryl groups include phenyl, pyridyl, imidazolyl and pyrrolyl groups. An example of the arylalkenyl groups is 2-(4-pyridyl)vinyl group. Dialkylamidino groups include N,N-dialkylamidino groups and N,N'-dialkylamidino groups. The two alkyl groups in the dialkylcarbamoyl groups, dialkylamidino groups, trialkylamidino groups, dialkylamino groups, dialkylaminoalkyl groups, dialkylaminosulfonyl groups and dialkylguanidino groups may be bonded together to form a ring. In those groups, one of $CH_2$'s may be replaced with O, NH or S. For example, dialkylcarbamoyl groups include, for example, 1-pyrrolidinecarbonyl group; dialkylamidino groups include, for example, 2-imidazoline-2-yl group and (pyrrolidine-1-yl)(imino)methyl group; and dialkylguanidino groups include, for example, imidazoline-2-amino group. The acyl groups includes not only alkylcarbonyl groups but also arylcarbonyl groups. For example, the acyl groups having 1 to 8 carbon atoms include benzoyl group. The alkoxyl groups include, for example, cyclohexyloxy group and phenoxyl group. The alkoxycarbonyl groups include benzyloxycarbonyl group, etc.

The compounds of the present invention may have an asymmetric carbon atom. These compounds include mixtures of various stereoisomers such as geometrical isomers, tautomers and optical isomers, and these isolated therefrom.

In the above-described compounds, those of general formula (1) wherein A represents an organic group of formula (2) are particularly preferred in the present invention.

In general formula (2), V is preferably an alkanesulfonyl group having 1 to 6 carbon atoms, which may have a substituent, or a benzoyl, benzenesulfonyl, 2-naphthalenesulfonyl, cinnamoyl, piperidinecarbonyl, phenylacetyl, pyridinecarbonyl, thiophenecarbonyl, phenylthiocarbonyl or benzimidoyl group which may have a substituent. V is more preferably a benzoyl group which may have a substituent, piperidinecarbonyl group which may have a substituent or pyridinecarbonyl group which may have a substituent. V is still more preferably the benzoyl group having a substituent or piperidinecarbonyl group having a substituent.

When V in formula (2) has a substituent, the substituent is selected from among 4-piperydyloxy group, 1-acetimidoyl-4-piperidyloxy group, dimethylcarbamoyl group, N,N-dimethylamidino group, 1-pyrrolidinecarbonyl group, 2-(4-pyridyl)ethyl group, 4-imino(pyrrolidine-1-yl) group, benzoyl group or 4-pyridyl group. Guanidino group is also preferred.

L in general formula (2) is preferably a group of any of formulae (3) to (5), particularly formula (3). When X has a substituent, the substituent is, for example, benzyloxycarbonyl group, carboxyl group, methoxycarbonyl group, ethoxycarbonyl group, ethanesulfonyloxy group, butanesulfonyloxy group, 4-piperidyloxy group, 1-acetimidoyl-4-piperidyloxy group, 1-benzyloxycarbonyl-4-piperidyloxy group, 4-piperidylmethyl group, (1-acetimidoyl-4-piperidyl)methyl group, 1-acetimidoyl-3-pyrrolidyloxy group, isopropyl group, 3-indolyl group or iodine atom.

It is preferred that W in the formula represents a hydrogen atom or an alkyl group having 1 to 6 carbon atoms and X represents a hydrogen atom, a carboxyalkyl group having 2 or 3 carbon atoms or an alkoxycarbonylalkyl group having 3 to 10 carbon atoms. It is more preferred that W represents a hydrogen atom, and X represents a hydrogen atom, carboxyethyl group or ethoxycarbonylethyl group.

It is more preferred that Y in general formula (2) represents a group of formula (7) wherein n is an integer of 1.

It is preferred that in general formula (1), Z represents a hydrogen atom, an alkyl group having 1 to 6 carbon atoms, a halogeno group or a group of formula (14) or (15), n in formula (14) represents an integer of 1 or 2, and $R^2$ represents a hydroxyl group, carboxyl group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms. It is more preferred that Z represents a hydrogen atom or a group of formula (14), and $R^2$ represents a hydroxyl group, a carboxyl group or an alkoxycarbonyl group having 2 to 7 carbon atoms. $R^2$ is particularly preferably a carboxyl group.

Preferably, Z represents a group of formula (15) wherein $R^3$ represents a hydroxyl group, a carboxyl group or an alkoxycarbonyl group having 2 to 7 carbon atoms, and $R^4$ represents a hydroxyl group. $R^3$ is particularly preferably a carboxyl group.

Z is preferably a hydrogen atom, iodine atom, methyl group or 2-carboxy-2-oxoethyl group.

The oil-soluble organic group B or B' in general formula (20) imparts an effect of inhibiting the activated blood coagulation factor X to the compound of general formula (20). In the present invention, B is preferably an oil-soluble organic group and B' is preferably a hydrogen atom.

The oil-soluble organic groups are those having a bonding group capable of bonding to an isoquinoline ring, a terminal aromatic group and/or a heterocyclic group. They are organic groups which are, as a whole, soluble in an oil. The bonding groups herein include aliphatic organic groups, which may contain an oxygen atom or nitrogen atom, such as alkylene groups and hydroxyalkylene groups. The terminal aromatic groups and/or heterocyclic groups include phenyl group, naphthyl group, piperidine group, pyridine group, etc. The oil-soluble organic groups are preferably those represented by above formula (2).

The fact whether a compound of general formula (20) actually has an inhibiting effect on the activated blood coagulation factor X can be easily known by a method described in Examples given below.

Typical processes for producing compounds (1) and (20) of the present invention are as follows:

An aminoisoquinoline derivative (23) can be obtained by reacting an aminoalkyl halide (21), in which nitrogen is protected with benzyloxycarbonyl group, t-butoxycarbonyl group or the like, with a 1-aminoisoquinoline (22) having a hydroxyl group at the 5, 6 or 7 position in the presence of a base such as potassium carbonate in a solvent such as dimethylformamide. The protecting group on the nitrogen of the obtained aminoisoquinoline derivative (23) can be removed in, for example, an acidic solution such as 4 N solution of hydrogen chloride in dioxane to obtain a corresponding amine (24).

The aminoalkyl halide (21) can be obtained also by, for example, replacing carboxyl group of the amino acid having non-protected N atom. Hydroxyisoquinolines can be synthesized by, for example, methods shown in Examples 1 and 2.

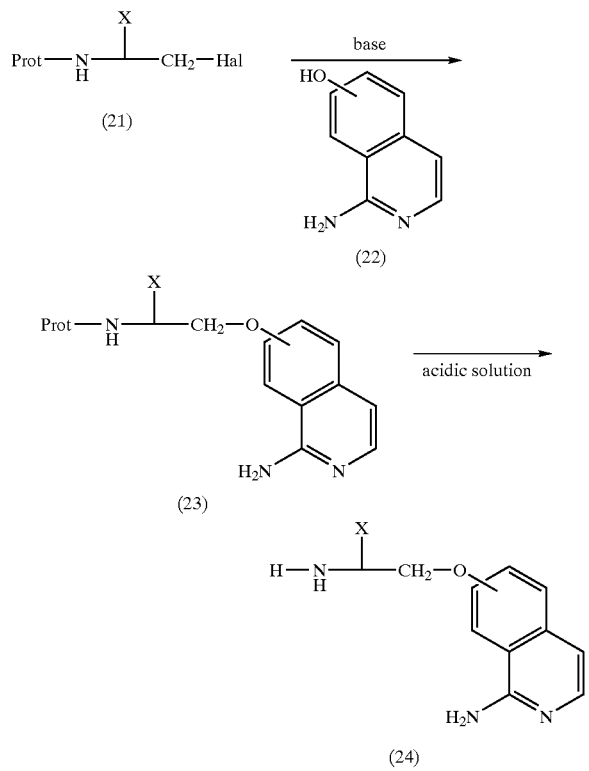

Prot in the above formulae represents a protecting group such as Boc group or Z group, and Hal represents a halogen atom.

Then, the amine (24) is reacted with a condensing agent in the presence of a base such as triethylamine in a solvent such as dimethylformamide. The amine is thus condensed with a carboxylic acid, or it is sulfonylated by the reaction with a sulfonyl halide. Thus, an aminoisoquinoline derivative (25) of general formula (1) wherein A or A' represents an organic group (2) in which Y is represented by above formula (7) and L is represented by above formula (3), and Z represents a hydrogen atom can be obtained.

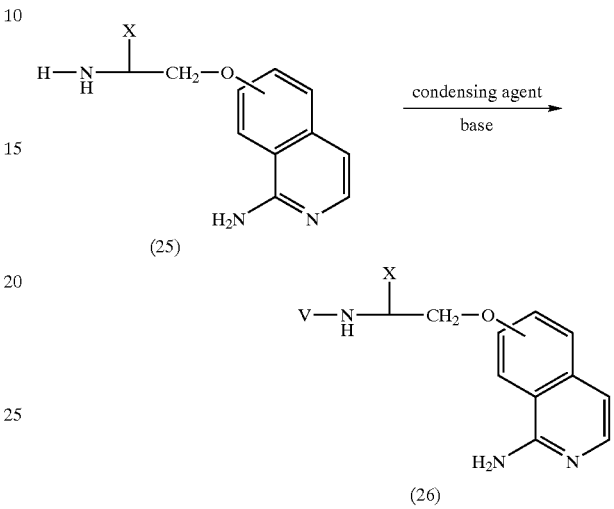

The compounds of general formulae (1) and (20) produced as described above and salts thereof can be isolated by the purification by a well-known method such as extraction, concentration, concentration under reduced pressure, extraction with a solvent, crystallization, recrystallization, redissolution or various chromatographic techniques.

The salts of aminoisoquinoline derivatives represented by general formulae (1) and (2) are pharmaceutically acceptable ones such as salts of them with mineral acids, e.g. hydrochloric acid, hydrobromic acid, sulfuric acid, nitric acid and phosphoric acid; and organic acids, e.g. formic acid, acetic acid, lactic acid, salicylic acid, mandelic acid, citric acid, oxalic acid, maleic acid, fumaric acid, tartaric acid, tannic acid, malic acid, toluenesulfonic acid, methanesulfonic acid and benzenesulfonic acid.

The compounds of general formulae (1) and (20) and salts thereof are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method. For example, the tablets are prepared by mixing the aminoisoquinoline derivative, the active ingredient of the present invention, with any of known adjuvants such as inert diluents, e.g. lactose, calcium carbonate and calcium phosphate, binders, e.g. acacia, corn starch and gelatin, extending agents, e.g. alginic acid, corn starch and pregelatinized starch, sweetening agents, e.g. sucrose, lactose and saccharin, corrigents, e.g. peppermint and cherry, and lubricants, e.g. magnesium stearate, talc and carboxymethyl cellulose.

When the aminoisoquinoline derivatives of general formulae (1) and (20) are used as the anticoagulants, they can be administered either orally or parenterally. The dose which varies depending on the age, body weight and conditions of the patient and the administration method is usually 0.01 to 1,000 mg, preferably 0.1 to 50 mg, a day for adults in the oral administration, and 1 μg to 100 mg, preferably 0.01 to 10 mg, in the parenteral administration.

The following Examples will further illustrate the present invention, which are only preferred embodiments of the invention and which by no means limit the invention.

EXAMPLE 1

Synthesis of N-[2-(1-aminoisoquinoline-5-yloxy) ethyl]-4-(1-pyrrolidinecarbonyl)benzamide mono-trifluoroacetate Step 1: Synthesis of 5-methoxyisoquinoline:

5.6 g (38.6 mmol) of 5-hydroxyisoquinoline was dissolved in 70 ml of DMF. 2.63 ml (38.6 mmol) of methyl iodide and 7.99 g (57.9 mmol) of potassium carbonate were added to the obtained solution, and they were stirred at room temperature overnight. After the treatment with ethyl acetate as the extracting solvent in an ordinary manner, the crude product was obtained. It was purified by the silica gel column chromatography to obtain the title compound.

Yield: 2.5 g (15.7 mmol) (41%)

H-NMR (CDCl$_3$) δ 4.00 (3H, s), 6.99 (1H, dd), 7.50 (2H, d), 7.98 (1H, d), 8.48 (1H, d), 9.10 (1H, s)

Step 2: Synthesis of 1-amino-5-hydroxyisoquinoline monohydrobromide:

900 mg (5.66 mmol) of 5-methoxyisoquinoline was dissolved in 20 ml of xylene. 4.26 ml (28.3 mmol) of N,N,N',N'-tetramethylenediamine and 1.17 g (30.0 mmol) of sodium amide were added to the obtained solution, and they were stirred at 140° C. for 1 hour. After the treatment with ethyl acetate as the extraction solvent in an ordinary manner, 10 ml of hydrobromic acid was added to the obtained crude product and they were heated under reflux for 6 hours. The solvent was evaporated to obtain the title compound.

Yield: 240 mg (1.0 mmol)

Step 3: Synthesis of t-butyl (2-chloroethyl)carbamate:

28.7 g (249 mmol) of 2-chloroethylamine hydrochloride was dissolved in 300 ml of dichloromethane. 41 g (192 mmol) of di-t-butyl dicarbonate and 80 ml (576 mmol) of triethylamine were added to the obtained solution, and they were stirred overnight. After the treatment with dichloromethane as the extraction solvent in an ordinary manner, the title compound was obtained.

Yield: 41 g (229 mmol) (92%)

H-NMR (CDCl$_3$) δ 1.43 (9H, s), 3.41 (2H, dt), 3.59 (2H, t), 4.95 (1H, br)

Step 4: Synthesis of t-butyl[2-(1-aminoisoquinoline-5-yloxy)ethyl]carbamate mono-trifluoroacetate:

240 mg (1.0 mmol) of 1-amino-5-hydroxyisoquinoline monohydrobromide was dissolved in 10 ml of DMF. 197 mg (1.16 mmol) of t-butyl (2-chloroethyl)carbamate, 382 mg (2.76 mmol) of potassium carbonate and 71 mg (0.45 mmol) of potassium iodide were added to the obtained solution. They were stirred at 70° C. for 3 days. After the treatment with dichloromethane as the extraction solvent in an ordinary manner, the obtained crude product was subjected to reversed phase high performance liquid chromatography with silica gel chemically bonded with octadodecyl group. After the elution with a mixed solution of water and acetonitrile containing 0.1% (v/v) of trifluoroacetic acid, the intended fraction was freeze-dried to obtain the title compound.

Yield: 34 mg (0.082 mmol) (9%)

H-NMR (CDCl$_3$) δ 1.44 (9H, s), 3.66 (2H, dt), 4.19 (2H, t), 7.26 (1H, d), 7.44 (2H, br), 7.58 (1H, t), 7.90 (1H, d)

Step 5: Synthesis of 4-(1-pyrrolidylcarbonyl)benzoic acid:

29.0 g (0.146 mol) of monomethyl terephthalate chloride was reacted with 14.2 g (200 mmol) of pyrrolidine and 21.0 g (208 mmol) of triethylamine in 350 ml of dichloromethane. After the treatment in an ordinary manner, methyl 4-(1-pyrrolidylcarbonyl)benzoate was obtained. 29.0 g of the ester was hydrolyzed with 12.0 g of sodium hydroxide in a mixed solvent comprising 70 ml of water, 70 ml of methanol and 70 ml of tetrahydrofuran. After the completion of the reaction, the solvent was evaporated. 1 N hydrochloric acid was added to the residue and the obtained mixture was treated with dichloromethane as the extraction solvent in an ordinary manner to obtain the title compound.

Yield: 23.7 g (108 mmol)

H-NMR (DMSO-d6) δ 1.75–1.90 (4H, m), 3.30–3.50 (4H, m), 7.62 (2H, d), 7.99 (2H, d), 13.14 (1H, br)

Step 6: Synthesis of [2-(1-aminoisoquinoline-5-yloxy) ethyl]-4-(1-pyrrolidinecarbonyl)benzamide monotrifluoroacetate:

34 mg (0.082 mmol) of t-butyl[2-(1-aminoisoquinoline-5-yloxy)ethyl]carbamate mono-trifluoroacetate was dissolved in a mixture of 1 ml of a 4 N solution of hydrogen chloride in dioxane and 1 ml of dioxane. The obtained solution was stirred at room temperature for one hour. The solvent was evaporated under reduced pressure, and the obtained crude product was dissolved in 5 ml of DMF. 25 mg (0.11 mmol) of 4-(1-pyrrolidinecarbonyl)benzoic acid, 21 mg (0.11 mmol) of 1-(3-dimethylaminopropyl)-3-ethylcarbodiimide hydrochloride, 15 mg (0.11 mmol) of 1-hydroxybenzotriazole and 0.03 ml (0.22 mmol) of triethylamine were added to the solution, and the obtained mixture was stirred at room temperature overnight. After the same procedure as that in step 4 in Example 1, the title compound was obtained.

Yield: 27 mg (0.052 mmol) (64%).

MS (ESI, m/z) 405 (MH+)

H-NMR (DMSO-d6) δ 1.74–1.95 (4H, m), 3.27–3.36 (2H, m), 3.43–3.52 (2H, m), 3.78 (2H, dt), 4.33 (2H, t), 7.46 (1H, d), 7.54 (1H, d), 7.59(2H, d),7.67 (1H, d), 7.73 (1H, d), 7.90 (2H, d), 8.08 (1H, d), 8.88 (1H, t), 9.02 (2H, br)

EXAMPLE 2

Synthesis of N-[2-(1-aminoisoquinoline-7-yloxy) ethyl]-4-(1-pyrrolidinecarbonyl)benzamide mono-trifluoroacetate Step 1: Synthesis of N-(2,2-dimethoxyethyl)-4-methylbenzenesulfonamide:

5.25 g (50 mmol) of aminoacetaldehyde dimethylacetal was dissolved in 400 ml of tetrahydrofuran. 106 g (1 mol) of sodium carbonate and 11.44 g (60 mmol) of p-toluenesulfonyl chloride were added to the obtained solution. They were stirred for 3 days and then treated with dichloromethane as the extracting solvent in an ordinary manner to obtain the title compound. After the purification by the silica gel column chromatography, the title compound was obtained.

Yield: 13.0 g (50 mmol) (100%)

H-NMR (CDCl$_3$) δ 2.40 (3H, s), 3.02 (2H, t), 3.30 (6H, s), 4.31 (1H, t),7.27 (2H, d), 7.72 (2H, d)

Step 2: Synthesis of N-(2,2-dimethoxyethyl)-N-(3-methoxybenzyl)-4-methylbenzenesulfonamide:

13.0 g (50 mmol) of N-(2,2-dimethoxyethyl)-4-methylbenzenesulfonamide was dissolved in 40 ml of DMF. 2.01 g (50 mmol) of sodium hydride was added to the obtained solution at room temperature. After stirring for 10 minutes, 9.18 g (46 mmol) of 3-methoxybenzyl bromide was added to the obtained mixture, and they were stirred for 2 hours. After the treatment with ethyl acetate as the extraction solvent in an ordinary manner, the obtained crude product was purified by the silica gel column chromatography to obtain the title compound.

Yield: 17.8 g (45 mmol) (99%)

H-NMR (CDCl₃) δ 2.40 (3H, s), 3.20 (2H, d), 3.22 (6H, s), 3.70 (3H, s), 4.37 (1H, t), 4.43 (2H, s), 6.67–6.71 (1H, m), 6.76 (2H, dd), 7.16 (1H, t), 7.28 (2H, d), 7.72 (2H, d)

Step 3: Synthesis of 7-methoxyisoquinoline:

17.8 g (45 mmol) of N-(2,2-dimethoxyethyl)-N-(3-methoxybenzyl)-4-methylbenzenesulfonamide was dissolved in 250 ml of dioxane and 70 ml of 6 N hydrochloric acid. After heating under reflux for 5 hours, the product was treated with ethyl acetate as the extracting solvent in an ordinary manner to obtain the crude product, which was purified according to the silica gel column chromatography to obtain the title compound.

Yield: 6.6 g (41 mmol) (91%)

H-NMR (CDCl₃) δ 3.94 (3H, s), 7.20 (1H, d), 7.34 (1H, dd), 7.57 (1H, d), 7.70 (1H, d), 8.40 (1H, d), 9.16 (1H, d)

Step 4 Synthesis of 1-amino-7-hydroxyisoquinoline monohydrobromide:

5.6 g (35.2 mmol) of 7-methoxyisoquinoline was dissolved in 200 ml of xylene. 26.6 ml (176 mmol) of N,N,N',N'-tetramethylenediamine and 7.28 g (186 mmol) of sodium amide were added to the obtained solution, and they were stirred at 140° C. for 1 hour. After the treatment with ethyl acetate as the extracting solvent in an ordinary manner, 50 ml of hydrobromic acid was added to the obtained crude product and they were stirred at 140° C. overnight. The solvent was evaporated to obtain the title compound.

Yield: 10 g

Step 5: Synthesis of t-butyl [2-(1-aminoisoquinoline-7-yloxy)ethyl] carbamate:

6.18 g (19.2 mmol) of 1-amino-7-hydroxyisoquinoline monohydrobromide was dissolved in 75 ml of DMF. 5.15 g (28.8 mmol) of t-butyl (2-chloroethyl)carbonate, 13.2 g (96.0 mmol) of potassium carbonate and 7.0 g (19.2 mmol) of tetrabutylammonium iodide were added to the obtained solution, and they were stirred at 70° C. for 3 days. After the treatment with dichloromethane as the extraction solvent in an ordinary manner, the crude product was obtained, which was purified by the silica gel column chromatography to obtain the title compound.

Yield: 3.5 g (11.6 mmol) (60%)

H-NMR (CDCl₃) δ 1.43 (9H, s), 3.57 (2H, dt), 4.18 (2H, t), 6.97 (1H, d), 7.24 (1H, dd), 7.35 (1H, br), 7.59 (1H, d), 7.77 (1H, d)

Step 6: Synthesis of [2-(1-aminoisoquinoline-7-yloxy)ethyl]-4-(1-pyrrolidinecarbonyl)benzamide monotrifluoroacetate:

800 mg (2.67 mmol) of t-butyl[2-(1-aminoisoquinoline-7-yloxy)ethyl]carbamate was dissolved in a mixture of 5 ml of a 4 N solution of hydrogen chloride in dioxane and 10 ml of dioxane. The obtained solution was stirred at room temperature for one hour. The solvent was evaporated under reduced pressure, and the obtained crude product was dissolved in 10 ml of DMF. 644 mg (2.91 mmol) of 4-(1-pyrrolidinecarbonyl)benzoic acid, 557 mg (2.91 mmol) of 1-(3-dimethylaminopropyl)-3-ethylcarbodiimide hydrochloride, 393 mg (2.91 mmol) of 1-hydroxybenzotriazole and 0.744 ml (5.34 mmol) of triethylamine were added to the solution, and the obtained mixture was stirred at room temperature overnight. After the same procedure as that in step 4 in Example 1, the title compound was obtained.

Yield: 1.1 g (2.12 mmol) (80%).

MS (ESI, m/z) 405 (MH+)

H-NMR (DMSO-d6) δ 1.74–1.93 (4H, m), 3.36–3.60 (4H, m), 3.75 (2H, dt), 4.31 (2H, t), 7.22 (1H, d), 7.57 (1H, d), 7.59 (2H, d), 7.63 (1H, dd), 7.92 (3H, d), 8.02 (1H, d), 8.90 (3H, br)

EXAMPLE 3

Synthesis of N-[2-(1-aminoisoquinoline-7-yloxy)ethyl]-4-(N,N-dimethylcarbamoyl)benzamide monotrifluoroacetate Step 1: Synthesis of 4-dimethylcarbamoylbenzoic acid:

A solution of 5 g (25.2 mmol) of monomethyl terephthalate chloride in 20 ml of dioxane was dissolved in 30 ml of 50% aqueous dimethylamine solution under cooling with ice. After stirring for 30 minutes, 50 ml of 1 N aqueous sodium hydroxide solution was added to the reaction mixture, and they were stirred at room temperature for 2 days. The reaction liquid was washed with ethyl acetate and acidified with hydrochloric acid. After the extraction with ethyl acetate, the extract was washed with saturated aqueous salt solution and then dried over anhydrous magnesium sulfate. The solvent was evaporated, and the residue was washed with hexane and dried to obtain the title compound.

Yield: 2.58 g (13.4 mmol) (53%)

H-NMR (CDCl₃)δ 2.85 (3H, br), 2.95 (3H, br), 7.50 (2H, d), 7.97 (2H, d)

Step 2 327 mg (1.08 mmol) of t-butyl [2-(1-aminoisoquinoline-5-yloxy)ethyl]carbamate was dissolved in a mixture of 2.5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 5 ml of DMF. 224 mg (1.13 mmol) of 4-(N,N-dimethylcarbamoyl)benzoic acid, 221 mg (1.13 mmol) of 1-(3-dimethylaminopropyl)-3-ethylcarbodiimide hydrochloride, 161 mg (1.13 mmol) of 1-hydroxybenzotriazole and 0.472 ml (3.39 mmol) of triethylamine were added to the obtained solution, and they were stirred at room temperature overnight. The title compound was obtained in the same manner as in step 4 in Example 1.

Yield: 130 mg (0.264 mmol) (24%)

MS (ESI, m/z) 379 (MH+)

H-NMR (DMSO-d6) δ 2.88 (3H, s), 2.99 (3H, s), 3.75 (2H, dt), 4.31 (2H,t), 7.21 (1H, d), 7.48 (2H, d), 7.57 (1H, d), 7.62 (1H, dd), 7.92 (3H, d), 8.02 (1H, d), 8.84–8.98 (3H, m)

EXAMPLE 4

Synthesis of ethyl N-[2-(1-aminoisoquinoline-7-yloxy)ethyl]-4-(4-piperidyloxy)benzamide bistrifluoroacetate Step 1: Synthesis of ethyl 4-(1-t-butoxycarbonyl-4-piperidyloxy)benzoate:

1.76 g (9.3 mmol) of 1-t-butoxycarbonyl-4-hydroxypiperidine, obtained by t-butoxycarbonylating 4-hydroxypiperidine with di-t-butyl dicarbonate, 1.7 g (10.2 mmol) of ethyl 4-hydroxybenzoate and 2.44 g (9.3 mmol) of triphenylphosphine were dissolved in 40 ml of tetrahydrofuran. 1.62 g (9.3 mmol) of diethyl azodicarboxylate was added to the obtained solution, and they were stirred overnight. The reaction mixture was treated with ethyl acetate as the extraction solvent in an ordinary manner to obtain the crude product, which was purified by the silica gel column chromatography to obtain the title compound.

Yield: 1.57 g (4.5 mmol) (44%)

H-NMR (CDCl₃) δ 1.38 (3H, t), 1.50 (9H, s)1.70–1.80 (2H, m), 1.90–2.00 (2H, m), 3.30–3.41 (2H, m), 3.63–3.75 (2H, m), 4.35 (2H, q), 4.55 (1H, m), 6.90 (2H, d), 8.00 (2H, d)

Step 2: Synthesis of 4-(1-t-butoxycarbonyl-4-piperidyloxy) benzoic acid:

847 mg (2.43 mmol) of ethyl (1-t-butoxycarbonyl-4-piperidyloxy)benzoate was dissolved in 50 ml of ethanol. 5 ml of 1 N sodium hydroxide solution was added to the obtained solution, and they were stirred at room temperature for 3 days. The reaction solution was concentrated and then treated with ethyl acetate as the extraction solvent in an ordinary manner to obtain the title compound.

Yield: 697 mg (2.2 mmol) (92%)

H-NMR(CDCl$_3$) δ 1.50 (9H, s), 1.70–2.00 (4H, m), 3.30–3.40 (2H, m), 3.65–3.75 (2H, m), 4.60 (1H, s), 6.95 (2H, d), 8.05 (2H, d)

Step 3: Synthesis of N-[2-(1-aminoisoquinoline-7-yloxy) ethyl]-4-(4-piperidyloxy)benzamide bistrifluoroacetate:

Step 1: Synthesis of ethyl 4-(1-t-butoxycarbonyl-4-piperidyloxy)benzoate:

648 mg (2.15 mmol) of t-butyl [2-(1-aminoisoquinoline-7-yloxy)ethyl]carbamate was dissolved in a mixture of 2.5 ml of 4 N solution of hydrogen chloride in dioxane and 5 ml of dioxane. The obtained solution was stirred at room temperature overnight. The solvent was evaporated, and the residue was dissolved in 10 ml of DMF. 752 mg (2.36 mmol) of 4-(1-t-butoxycarbonyl-4-piperidyloxy)benzoic acid, 451 mg (2.36 mmol) of 1-(3-dimethylaminopropyl)-3-ethylcarbodiimide hydrochloride, 319 mg (2.36 mmol) of 1-hydroxybenzotriazole and 0.99 ml (7.08 mmol) of triethylamine were added to the obtained solution, and they were stirred at room temperature overnight. The reaction mixture was treated with dichloromethane as the extracting solvent in an ordinary manner, and the obtained crude product was dissolved in a mixture of 2 ml of 4 N solution of hydrogen chloride in dioxane and 1 ml of dioxane. The obtained solution was stirred at room temperature overnight. The title compound was obtained in the same manner as that in step 4 in Example 1.

Yield: 220 mg (0.347 mmol) (16%)

MS (ESI, m/z) 407 (MH+)

H-NMR (DMSO-d6) δ 1.73–1.90 (2H, m), 2.04–2.18 (2H, m), 3.03–3.17 (2H,m), 3.20–3.34 (2H, m), 3.71 (2H, dt), 4.28 (2H, t), 7.07 (2H, d), 7.21 (1H, d), 7.58 (1H, d), 7.62 (1H, dd), 7.86 (2H, d), 7.91 (1H, d), 8.02 (1H, d), 8.50–8.71 (2H, m), 8.97 (3H, br)

EXAMPLE 5

Synthesis of N-[2-(1-aminoisoquinoline-7-yloxy) ethyl]-4-(1-acetimidoyl-4-piperidyloxy)benzamide bistrifluoroacetate 120 mg (0.231 mmol) of N-[2-(1-aminoisoquinoline-7-yloxy)ethyl]-4-(4-piperidyloxy)benzamide bistrifluoroacetate was dissolved in 10 ml of ethanol. 142 mg (1.15 mmol) of ethyl acetimidate hydrochloride and 0.322 ml (2.31 mmol) of triethylamine were added to the obtained solution, and they were stirred at room temperature overnight. The title compound was obtained after the same procedure as that in step 4 in Example 1.

Yield: 99 mg (0.147 mmol) (77%)

MS (ESI, m/z) 448 (MH+)

H-NMR (DMSO-d6) δ 1.69–1.77 (2H, m), 2.02–2.15 (2H, m), 2.30 (3H, s), 3.46–3.60 (2H, m), 3.68–3.86 (4H, m), 7.08 (2H, d), 7.22 (1H, d), 7.58 (2H,d), 7.62 (1H, dd), 7.87 (2H, d), 7.92 (1H, d), 8.01 (1H, br), 8.56–8.72 (2H, m), 8.99 (3H, br), 9.15 (1H, br)

EXAMPLE 6

Synthesis of N-[2-(1-aminoisoquinoline-7-yloxy) ethyl]-4-(N,N-dimethylamidino)benzamide bistrifluoroacetate Step 1: Synthesis of ethyl 4-(N,N-dimethylamidino) benzoate:

1 g (3.9 mmol) of ethyl 4-ethoxycarbonimidoylbenzoate hydrochloride was stirred in a mixture of 3 ml of ethanol and 10 ml of 50% aqueous dimethylamine solution overnight. The solvent was evaporated, and 10 ml of dioxane containing 4 N hydrogen chloride and 1 ml of ethanol were added to the residue. They were stirred at room temperature for 5 days, and the solvent was evaporated. 1 N sodium hydroxide was added to the residue. After the extraction with dichloromethane, the organic layer was washed with saturated aqueous common salt solution and then dried over anhydrous magnesium sulfate. The solvent was evaporated to obtain the title compound.

Yield: 671 mg (3.05 mmol) (78%)

H-NMR (CDCl$_3$)δ 1.40 (3H,t),2.95 (6H,s),4.30 (1H,br), 4.40(2H,q), 7.40 (2H,d),8.10 (2H,d)

Step 2: Synthesis of 4-(N,N-dimethylamidino)benzoic acid hydrochloride:

Ethyl 4-(N,N-dimethylamidino)benzoate and 6 N hydrochloric acid were heated under reflux for 6 hours and then the solvent was evaporated to obtain the title compound.

H-NMR (DMSO-d6) δ 2.95 (3H, s), 3.25 (3H, s), 7.75 (2H, d), 8.15 (2H, d), 9.25 (1H, br), 9.50 (1H, br)

Step 3: Synthesis of N-[2-(1-aminoisoquinoline-7-yloxy) ethyl]-4-(N,N-dimethylamidino)benzamide bistrifluoroacetate:

1.0 g (3.32 mmol) of t-butyl [2-(1-aminoisoquinoline-5-yloxy)ethyl]carbamate was dissolved in a mixture of 2.5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 757 mg (3.32 mmol) of 4-(N,N-dimethylamidino)benzoic acid monohydrochloride, 634 mg (3.32 mmol) of 1-(3-dimethylaminopropyl)-3-ethylcarbodiimide hydrochloride, 449 mg (3.32 mmol) of 1-hydroxybenzotriazole and 0.555 ml (3.99 mmol) of triethylamine were added to the obtained solution, and they were stirred at room temperature overnight. The title compound was obtained in the same manner as that in step 4 in Example 1.

Yield: 350 mg (0.579 mmol) (17%)

MS (ESI, m/z) 378 (MH+)

H-NMR (DMSO-d6) δ 2.96 (3H, s), 3.23 (3H, s), 3.78 (2H, dt), 4.32 (2H,t), 7.22 (1H, d), 7.59 (2H, d), 7.62 (1H, dd), 7.66 (2H, d), 7.92 (1H, d), 8.03 (1H, d), 8.07 (2H, d), 9.03 (4H, br), 9.37 (1H, br)

EXAMPLE 7

Synthesis of N-[2-(1-aminoisoquinoline-7-yloxy) ethyl]-4-[imino(pyrrolidine-1-yl)]benzamide bistrifluoroacetate Step 1: Synthesis of 4-[imino(pyrrolidine-1-yl)]benzoic acid hydrochloride:

15.2 g (103 mmol) of 4-cyanobenzoic acid was added to a mixture of a solution of 4 N hydrogen chloride in 200 ml of ethyl acetate and 50 ml of ethanol, and they were stirred for 5 days. The solvent was evaporated under reduced pressure. 100 ml of ethyl acetate was added to the obtained solid, and they were stirred for 30 minutes. The solid was taken by the filtration. The solid was reacted with 15.0 g (211 mmol) of pyrrolidine and 10.0 g (98.8 mmol) of triethylamine in 100 ml of ethanol as the solvent for two days. The solvent was evaporated. 40 ml of 6 N hydrochloric acid was added to the residue, and they were reacted at 85° C. for 4 hours. The solvent was evaporated, 50 ml of 1 N hydrochloric acid was added to the reaction mixture, and they were stirred for 30 minutes. The solid was taken by the filtration and then washed with 20 ml of ice/water. After the drying under reduced pressure, the title compound was obtained.

Yield: 7.67 g (30.1 mmol) (29.2%)

MS(ESI,m/z) 479(MH+)

H-NMR (DMSO-d6) δ 1.78–1.92 (2H, m), 1.98–2.12 (2H, m), 3.23–3.43 (2H, m),3.58–3.62(2H,m), 7.78(2H,d), 8.15(2H,d), 9.18(1H,bs), 9.45(1H,bs), 13.41(1H,bs)

Step 2: Synthesis of N-[2-(1-aminoisoquinoline-7-yloxy)ethyl]-4-[imino(pyrrolidine-1-yl)]benzamide bistrifluoroacetate:

A solution of 470 mg (1.56 mmol) of t-butyl [2-(1-aminoisoquinoline-5-yloxy)ethyl]carbamate in a mixture of 2.5 ml of 4 N solution of hydrogen chloride in dioxane and 5 ml of dioxane was stirred at room temperature for one hour. The solvent was evaporated under reduced pressure, and the obtained crude product was dissolved in 10 ml of DMF. 396 mg (1.56 mmol) of 4-[imino(pyrrolidine-1-yl)]benzoic acid monohydrochloride, 297 mg (1.56 mmol) of 1-(3-dimethylaminopropyl)-3-ethylcarbodiimide hydrochloride, 210 mg (1.56 mmol) of 1-hydroxybenzotriazole and 0.433 ml (3.11 mmol) of triethylamine were added to the obtained solution. They were stirred at room temperature overnight. The title compound was obtained in the same manner as that in step 4 in Example 1.

Yield: 280 mg (0.444 mmol) (28%)

MS (ESI, m/z) 404 (MH+)

H-NMR (DMSO-d6) δ 1.80–1.96 (2H, m), 2.00–2.14 (2H, m), 3.30–3.43 (2H,m), 3.53–3.64 (2H, m), 3.77 (2H, dt), 4.34 (2H, t), 7.21 (1H, d), 7.53 (1H, d), 7.58 (1H, dd), 7.60 (2H, d), 7.92 (1H, d), 8.03 (1H, d), 8.07 (2H, d), 8.88 (1H, br), 9.08 (3H, br), 9.37 (1H, br),

EXAMPLE 8

Synthesis of N-[2-(1-aminoisoquinoline-7-yloxy)ethyl]-[1-(4-pyridyl)-4-piperidine]carbamide bistrifluoroacetate Step 1: Synthesis of ethyl 1-(4-pyridyl)-piperidine-4-carboxylate:

4.0 g (26.6 mmol) of 4-chloropyridine hydrochloride, 4.2 g (26.6 mmol) of ethyl piperidine-4-carboxylate and 7.4 ml (53.2 mmol) of triethylamine were stirred in 100 ml of xylene at 130° C. for 24 hours. The reaction mixture was treated with ethyl acetate as the extraction solvent in an ordinary manner to obtain the title compound.

Yield: 2.95 g (12.6 mmol) (47%)

MS (ESI, m/z) 235 (MH+)

H-NMR (CDCl₃)δ 1.25 (3H, t), 1.71–1.85 (2H, m), 2.00 (2H, d), 2.05–2.60 (1H, m), 2.90 (2H, t), 3.81 (2H, d), 4.20 (2H, q), 6.66 (2H, d), 8.26 (2H, d)

Step 2: Synthesis of 1-(4-pyridyl)-4-piperidinecarboxylic acid hydrochloride:

2.95 g (12.6 mmol) of ethyl 1-(4-pyridyl)-piperidine-4-carboxylate was stirred in 100 ml of dioxane. After adding 50 ml of 1 N hydrochloric acid, the obtained mixture was stirred at 95° C. for 20 hours. The solvent was evaporated under reduced pressure to obtain the title compound.

Yield: 3.21 g (11.5 mmol) (91%)

MS (ESI, m/z) 207 (MH+)

H-NMR (DMSO-d6) δ 1.54 (2H, t), 1.90 (2H, d) 2.60–2.70 (1H, m), 3.30 (2H, t), 4.10 (2H, d), 7.19 (2H, d), 8.20 (2H, d)

Step 3: Synthesis of N-[2-(1-aminoisoquinoline-7-yloxy)ethyl]-[1-(4-pyridyl)-4-piperidine]carbamide bistrifluoroacetate:

A solution of 470 mg (1.56 mmol) of t-butyl [2-(1-aminoisoquinoline-5-yloxy)ethyl]carbamate in a mixture of 2.5 ml of 4 N solution of hydrogen chloride in dioxane and 5 ml of dioxane was stirred at room temperature for one hour. The solvent was evaporated under reduced pressure, and the obtained crude product was dissolved in 10 ml of DMF. 321 mg (1.56 mmol) of 1-(4-pyridyl)-4-piperidinecarboxylic acid, 297 mg (1.56 mmol) of 1-(3-dimethylaminopropyl)-3-ethylcarbodiimide hydrochloride, 210 mg (1.56 mmol) of 1-hydroxybenzotriazole and 0.433 ml (3.11 mmol) of triethylamine were added to the obtained solution. They were stirred at room temperature overnight. The title compound was obtained in the same manner as that in step 4 in Example 1.

Yield: 230 mg (0.371 mmol) (24%)

MS (ESI, m/z) 392 (MH+)

H-NMR (DMSO-d6) δ 1.46–1.67 (2H, m), 1.77–1.93 (2H, m), 2.56–2.65 (2H,m), 3.17–3.33 (2H, m), 3.58 (2H, dt), 4.07–4.30 (4H, m), 7.18 (2H, d), 7.21 (1H, d), 7.53 (1H, d), 7.59 (2H, dd), 8.21 (2H, d), 8.25 (1H, t), 9.00(2H, br)

EXAMPLE 9

Synthesis of N-[2-(1-aminoisoquinoline-7-yloxy)ethyl]-4-[2-(pyridine-4-yl)ethyl]benzamide bistrifluoroacetate Step 1: Synthesis of methyl 4-(diethoxyphosphorylmethyl)benzoate:

6.64 g (40 mmol) of triethyl phosphite was added to 2.29 g (10 mmol) of methyl 4-(bromomethyl)benzoate, and they were stirred at 150° C. for 19 hours. The reaction solution was treated by the silica gel column chromatography to obtain the title compound.

Yield: 2.6 g (9 mmol) (90%)

H-NMR (CDCl₃)δ 1.25 (6H, t), 3.20 (2H, d), 4.02 (4H, dq), 7.39 (2H, d), 8.00 (2H, d)

Step 2: Synthesis of 4-[2-(pyridine-4-yl)ethyl]benzoic acid hydrochloride:

4.80 g (16.8 mmol) of methyl 4-(diethoxyphosphorylmethyl)benzoate was dissolved in 100 ml of tetrahydrofuran. 620 mg (15.5 mmol) of sodium hydride was added to the obtained solution under cooling with ice, and the obtained mixture was stirred for 30 minutes and then stirred at room temperature for additional 30 minutes. 1.38 g (12.9 mmol) of pyridine-4-aldehyde was added to the mixture, and they were stirred for 20 hours. After the treatment with ethyl acetate as the extraction solvent in an ordinary manner, the obtained crude product was dissolved in 30 ml of methanol. 300 mg of 10% palladium-carbon was added to the obtained solution, and they were stirred in the presence of hydrogen for 20 hours. After the filtration through Celite, the solvent was evaporated. The residue was dissolved in 30 mol of concentrated hydrochloric acid, and the obtained solution was stirred at 40° C. overnight. The solvent was evaporated to obtain the crude title compound.

Yield: 2.7 g (11.9 mmol) (92%).

Step 3: Synthesis of N-[2-(1-aminoisoquinoline-7-yloxy)ethyl]-4-[2-(pyridine-4-yl)ethyl]benzamide bistrifluoroacetate:

420 mg (1.39 mmol) of t-butyl [2-(1-aminoisoquinoline-5-yloxy)ethyl]carbamate was dissolved in a mixture of 2.5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 316 mg (1.39 mmol) of 4-[2-pyridine-4-yl]ethyl]benzoic acid, 266 mg (1.39 mmol) of 1-(3-dimethylaminopropyl)-3-ethylcarbodiimide hydrochloride, 188 mg (1.39 mmol) of 1-hydroxybenzotriazole and 0.29 ml (2.09 mmol) of triethylamine were added to the obtained solution. The obtained mixture was stirred at room temperature overnight. The title compound was obtained in the same manner as that in step 4 in Example 1.

Yield: 260 mg (0.406 mmol) (29%)

MS (ESI, m/z) 413 (MH+)

H-NMR (DMSO-d6) δ 3.04 (2H, dd), 3.15 (2H, dd), 3.72 (2H, dt), 4.29 (2H,t),7.21 (1H, d), 7.34 (1H, d), 7.58 (1H, d), 7.62 (1H, dd), 7.76 (2H, d), 7.81 (2H, d), 7.92 (1H, d), 8.02 (1H, d), 8.72 (2H, d), 8.75 (1H, dd), 9.02 (2H, br)

EXAMPLE 10

Synthesis of N-[2-(1-aminoisoquinoline-7-yloxy)ethyl]-4-benzoylbanzamide mono-trifluoroacetate 890 mg (2.94 mmol) of t-butyl [2-(1-aminoisoquinoline-5-yloxy)ethyl]carbamate was dissolved in a mixture of 5 ml of 4 N solution of hydrogen chloride in dioxane and 15 ml of dioxane, and the obtained solution was stirred at room temperature for one hour. The solvent was evaporated under reduced pressure, and the obtained crude product was dissolved in 10 ml of DMF. 666 mg (2.94 mmol) of 4-benzoylbenzoic acid, 563 mg (2.94 mmol) of 1-(3-dimethylaminopropyl)-3-ethylcarbodiimide hydrochloride, 398 mg (2.94 mmol) of 1-hydroxybenzotriazole and 0.62 ml (4.42 mmol) of triethylamine were added to the obtained solution. They were stirred at room temperature overnight. The title compound was obtained in the same manner as that in step 4 in Example 1.

Yield: 650 mg (1.23 mmol) (32%)

MS (ESI, m/z) 412 (MH+)

H-NMR (DMSO-d6) δ 3.77 (2H, dt), 4.34 (2H, t), 7.21 (1H, d), 7.57 (2H, dd), 7.59 (1H, dd), 7.63 (1H, dd), 7.70 (1H, dd), 7.75 (2H, d), 7.81 (2H, d), 7.92 (1H, d), 8.02 (2H, d), 8.03 (1H, dd), 8.98 (2H, br), 9.02 (1H, t)

EXAMPLE 11

Synthesis of N-[3-(1-aminoisoquinoline-7-yloxy)propyl]-4-(1-pyrrolidinecarbonyl)benzamide mono-trifluoroacetate Step 1: Synthesis of t-butyl [3-(1-aminoisoquinoline-7-yloxy)propyl]carbamate:

4.0 g (12.7 mmol) of 1-amino-7-hydroxyisoquinoline monohydrobromide was dissolved in 50 ml of DMF. 4.42 g (18.6 mmol) of t-butyl (3-chloropropyl)carbamate, 8.76 g (63.5 mmol) of potassium carbonate and 4.69 g (12.7 mmol) of tetrabutylammonium iodide were added to the obtained solution, and they were stirred at 70° C. for 3 days. After the treatment with dichloromethane as the extraction solvent in an ordinary manner, the crude product was obtained, which was then purified by the silica gel column chromatography to obtain the title compound.

Yield: 2.1 g (6.65 mmol) (54%)

H-NMR (CDCl₃) δ 1.44 (9H, s), 1.93–2.10 (2H, m), 3.28–3.46 (2H, m), 4.21(2H, t), 6.97 (1H, d), 7.24 (1H, dd), 7.35 (1H, br), 7.59 (1H, d), 7.77 (1H, d)

Step 2: Synthesis of N-[3-(1-aminoisoquinoline-7-yloxy)propyl]-4-(1-pyrrolidinecarbonyl)benzamide mono-trifluoroacetate:

650 mg (2.06 mmol) of t-butyl [3-(1-aminoisoquinoline-7-yloxy)propyl]carbamate was dissolved in a mixture of 2.5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 500 mg (2.26 mmol) of 4-(1-pyrrolidinecarbonyl)benzoic acid, 432 mg (2.26 mmol) of 1-(3-dimethylaminopropyl)-3-ethylcarbodiimide hydrochloride, 305 mg (2.26 mmol) of 1-hydroxybenzotriazole and 0.86 ml (6.18 mmol) of triethylamine were added to the obtained solution. They were stirred at room temperature overnight. The title compound was obtained in the same manner as that in step 4 in Example 1.

Yield: 400 mg (0.752 mmol) (37%)

MS (ESI, m/z) 419 (MH+)

H-NMR (DMSO-d6) δ 1.75–1.93 (4H, m), 2.03–2.26 (2H, m), 3.35 (2H, dt), 3.42–3.55 (4H, m), 4.22 (2H, t), 7.22 (1H, d), 7.56 (1H, d), 7.58 (2H, d), 7.63 (1H, dd), 7.89 (2H, d), 7.92 (1H, d), 8.01 (1H, d), 8.68 (1H, t), 8.92 (2H, br)

EXAMPLE 12

Synthesis of N-[3-(1-aminoisoquinoline-7-yloxy)propyl]-4-(N,N-dimethylcarbamoyl)benzamide mono-trifluoroacetate 378 mg (1.20 mmol) of t-butyl [3-(1-aminoisoquinoline-7-yloxy)propyl]carbamate was dissolved in a mixture of 2.5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 254 mg (1.32 mmol) of 4-(1-pyrrolidinecarbonyl)benzoic acid, 251 mg (1.32 mmol) of 1-(3-dimethylaminopropyl)-3-ethylcarbodiimide hydrochloride, 118 mg (1.32 mmol) of 1-hydroxybenzotriazole and 0.50 ml (3.60 mmol) of triethylamine were added to the obtained solution. They were stirred at room temperature overnight. The title compound was obtained in the same manner as that in step 4 in Example 1.

Yield: 180 mg (0.356 mmol) (24%)

MS (ESI, m/z) 393 (MH+)

H-NMR (DMSO-d6) δ 2.04–2.16 (2H, m), 2.89 (3H, s), 3.00 (3H, s), 3.51 (2H, dt), 4.25 (2H, t), 7.22 (1H, d), 7.48 (2H, d), 7.58 (1H, d), 7.64 (1H, dd), 7.90 (2H, d), 7.93 (1H, d), 8.02 (1H, d), 8.68 (1H, t), 8.92 (2H, br)

EXAMPLE 13

Synthesis of N-[3-(1-aminoisoquinoline-7-yloxy)propyl]-4-(4-piperidyloxy)benzamide bistrifluoroacetate 720 mg (2.28 mmol) of t-butyl [3-(1-aminoisoquinoline-7-yloxy)propyl]carbamate was dissolved in a mixture of 2.5 ml of 4 N solution of hydrogen chloride in dioxane and 5 ml of dioxane, and the obtained solution was stirred at room temperature overnight. The solvent was evaporated, and the residue was dissolved in 10 ml of DMF. 805 mg (2.51 mmol) of 4-(1-t-butoxycarbonyl-4-piperidyloxy)benzoic acid, 479 mg (2.51 mmol) of 1-(3-dimethylaminopropyl)-3-ethylcarbodiimide hydrochloride, 339 mg (2.51 mmol) of 1-hydroxybenzotriazole and 0.95 ml (6.84 mmol) of triethylamine were added to the obtained solution. They were stirred at room temperature overnight. After the treatment with dichloromethane as the extraction solvent, the obtained crude product was dissolved in a mixture of 2 ml of 4 N solution of hydrogen chloride in dioxane and 1 ml of dioxane. The obtained solution was stirred at room temperature overnight. The title compound was obtained in the same manner as that in step 4 in Example 1.

Yield: 890 mg (1.67 mmol) (60%)

MS (ESI, m/z) 421 (MH+)

H-NMR (DMSO-d6) δ 1.83–1.99 (2H, m), 2.00–2.17 (4H, m), 3.03–3.17 (2H,m), 3.20–3.32 (2H, m), 3.46 (2H, dt), 4.21 (2H, t), 4.70–4.78 (1H, m), 7.05 (2H, d), 7.21 (1H, d), 7.57 (1H, d), 7.62 (1H, dd), 7.83 (2H, d), 7.92 (1H, d), 7.99 (1H, d), 8.46 (1H, t), 8.50–8.69 (2H, m), 8.99 (2H, br)

EXAMPLE 14

Synthesis of N-[3-(1-aminoisoquinoline-7-yloxy)propyl]-4-(1-acetimidoyl-4-piperidyloxy)benzamide bistrifluoroacetate 580 mg (1.09 mmol) of N-[3-(1-aminoisoquinoline-7-yloxy)propyl]-4-(4-piperidyloxy)benzamide bistrifluoroacetate was dissolved in 10 ml of ethanol. 500 mg (4.07 mmol) of ethyl acetimidate hydrochloride and 2 ml (14.3 mmol) of triethylamine were added to the obtained solution, and they were stirred at room temperature overnight. The title compound was obtained in the same manner as that in step 4 in Example 1.

Yield: 630 mg (1.09 mmol) (100%)

MS (ESI, m/z) 462 (MH+)

H-NMR (DMSO-d6) δ 1.64–1.90 (2H, m), 2.03–2.18 (4H, m), 2.29 (3H, s), 3.22–3.43 (4H, m), 3.70–3.82 (2H, m), 4.22 (2H, t), 4.74–4.88 (1H, m), 7.04(2H, d), 7.22 (1H, d), 7.58 (1H, d), 7.63 (1H, dd), 7.85 (2H, d), 7.93 (1H, d), 8.02 (1H, br), 8.46 (1H, t), 9.04 (2H, br), 9.19 (2H, br)

EXAMPLE 15

Synthesis of benzyl (4R)-5-(1-aminoisoquinoline-7-yloxy)-4-[4-(1-pyrrolidinecarbonyl)benzoylamino]pentanoate mono-trifluoroacetate Step 1: Synthesis of benzyl (4R)-4-t-butoxycarbonylamino-5-chloropentanoate:

25.0 g (74.2 mmol) of γ-benzyl N-t-butoxycarbonyl-D-glutamate was dissolved in a mixture of 8.15 ml (74.2 mmol) of N-methylmorpholine and 500 ml of tetrahydrofuran. 7.05 ml (74.2 mmol) of ethyl chloroformate was added to the obtained solution under cooling with ice, and they were stirred for 20 minutes. Precipitates thus formed were removed by the filtration under suction. 5 g of ice and 2.81 g (74.2 mmol) of sodium borohydride were added to the filtrate under cooling with ice, and they were stirred for 30 minutes. 20 ml of 1 N hydrochloric acid was added to the obtained mixture, and they were stirred at room temperature for one hour. After the treatment with ethyl acetate as the extraction solvent in an ordinary manner, the obtained crude product was dissolved in a mixture of 20.6 ml (148 mmol) of triethylamine and 100 ml of dichloromethane. 12.7 g (111 mmol) of methanesulfonyl chloride was added to the obtained solution under cooling with ice, and they were stirred for 2 hours. After the treatment with dichloromethane as the extraction solvent in an ordinary manner, the obtained crude product was dissolved in 250 ml of DMF. 15.5 g (371 mmol) of lithium chloride was added to the obtained solution, and they were stirred at 50° C. overnight. After the treatment with ethyl acetate as the extraction solvent in an ordinary manner, the obtained crude product was purified by the silica gel column chromatography to obtain the title compound.

Yield: 14.6 g (42.8 mmol) (58%)

H-NMR(CDCl$_3$) δ 1.41 (9H, s), 1.83–1.96 (2H, m), 2.44 (2H, dd), 3.52–3.69 (2H, m), 3.91 (1H, br), 4.72 (1H, br), 5.11 (2H, s), 7.28–7.36 (5H, m)

Step 2: Synthesis of benzyl (4R)-5-(1-aminoisoquinoline-7-yloxy)-4-t-butoxycarbonylaminopentanoate:

8.81 g (27 mmol) of 1-amino-7-hydroxyisoquinoline monohydrobromide was dissolved in 120 ml of DMF. 14.0 g (41 mmol) of benzyl (4R)-4-t-butoxycarbonylamino-5-chloropentanoate, 11.2 g (81.0 mmol) of potassium carbonate and 9.96 g (27 mmol) of tetrabutylammonium iodide were added to the obtained solution, and they were stirred at 70° C. for 3 days. After the treatment with dichloromethane as the extraction solvent in an ordinary manner, the obtained crude product was purified by the silica gel column chromatography to obtain the title compound.

Yield: 12.0 g (25.8 mmol) (94%)

H-NMR(CDCl$_3$) δ 1.43 (9H, s), 1.83–1.99 (2H, m), 2.50 (2H, dd), 3.88–4.18 (3H, m), 5.10 (2H, s), 6.94 (1H, d), 7.24–7.37 (6H, m), 7.46 (1H, br), 7.60 (1H, d), 7.80 (1H, d)

Step 3: Synthesis of benzyl (4R)-5-(1-aminoisoquinoline-7-yloxy)-4-[4-(1-pyrrolidinecarbonyl)benzoylamino]pentanoate mono-trifluoroacetate:

750 mg (1.61 mmol) of benzyl (4R)-5-(1-aminoisoquinoline-7-yloxy)-4-t-butoxycarbonylaminopentanoate was dissolved in a mixture of 5 ml of 4 N solution of hydrogen chloride in dioxane and 15 ml of dioxane. The obtained solution was stirred at room temperature for one hour. The solvent was evaporated under reduced pressure, and the obtained crude product was dissolved in 10 ml of DMF. 356 mg (1.61 mmol) of 4-(1-pyrrolidinecarbonyl)benzoic acid, 308 mg (1.61 mmol) of 1-(3-dimethylaminopropyl)-3-ethylcarbodiimide hydrochloride, 218 mg (1.61 mmol) of 1-hydroxybenzotriazole and 0.34 ml (2.42 mmol) of triethylamine were added to the obtained solution, and they were stirred at room temperature overnight. The title compound was obtained in the same manner as that in step 4 in Example 1.

Yield: 670 mg (1.16 mmol) (72%)

MS (ESI, m/z) 567 (MH+)

H-NMR (DMSO-d6) δ 1.71–2.04 (6H, m), 2.40–2.55 (2H, m), 3.33 (2H, dd), 3.46 (2H, dd), 4.10–4.30 (2H, m), 4.37–4.52 (1H, m), 5.07 (2H, s), 7.21 (1H, d), 7.29–7.39 (5H, m), 7.56 (1H, d), 7.60 (2H, d), 7.62 (1H, dd), 7.90 (1H, d), 7.92 (2H, d), 8.01 (1H, dd), 8.57 (1H, d), 8.92 (2H, br)

EXAMPLE 16

Synthesis of (4R)-5-(1-aminoisoquinoline-7-yloxy)-4-[4-(1-pyrrolidinecarbonyl)benzoylamino]pentanoic acid mono-trifluoroacetate 670 mg (1.16 mmol) of benzyl (4R)-5-(1-aminoisoquinoline-7-yloxy)-4-[4-(1-pyrrolidinecarbonyl)benzoylamino]pentanoate mono-trifluoroacetate was dissolved in 10 ml of concentrated hydrochloric acid, and the obtained solution was stirred at 40° C. for one hour.

The title compound was obtained in the same manner as that in step 4 in Example 1.

Yield: 450 mg (0.763 mmol) (66%)

MS (ESI, m/z) 567 (MH+)

H-NMR (DMSO-d6) δ 1.74–2.15 (6H, m), 2.33–2.44 (2H, m), 3.35 (2H, dd), 3.47 (2H, dd), 4.12–4.38 (2H, m), 4.35–4.50 (1H, m), 7.21 (1H, d), 7.57 (1H, d), 7.59 (2H, d), 7.63 (1H, dd), 7.90 (1H, d), 7.92 (2H, d), 8.01 (1H, d d), 8.54 (1H, d), 8.95 (2H, br)

EXAMPLE 17

Synthesis of ethyl (4R)-5-(1-aminoisoquinoline-7-yloxy)-4-[4-(1-pyrrolidinecarbonyl)benzoylamino]pentanoate mono-trifluoroacetate 800 mg (1.72 mmol) of benzyl (4R)-5-(1-aminoisoquinoline-7-yloxy)-4-t-butoxycarbonylaminopentanoate was dissolved in a mixture of 5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 312 mg (1.41 mmol) of 4-(1-pyrrolidinecarbonyl)benzoic acid, 270 mg (1.41 mmol) of 1-(3-dimethylaminopropyl)-3-ethylcarbodiimide hydrochloride, 191 mg (1.41 mmol) of 1-hydroxybenzotriazole and 0.34 ml (2.11 mmol) of triethylamine were added to the obtained solution, and they were stirred at room temperature overnight. After the treatment with dichloromethane as the extraction solvent in an ordinary manner, the obtained crude product was dissolved in a mixture of 20 ml of ethanol and 0.5 ml of concentrated sulfuric acid, and the obtained solution was refluxed under heating for 3 hours. The title compound was obtained in the same manner as that in step 4 in Example 1.

Yield: 320 mg (0.518 mmol) (30%)

MS (ESI, m/z) 505 (MH+)

H-NMR (DMSO-d6) δ 1.15 (3H, t), 1.77–1.80 (4H, m), 1.81–2.00 (1H, m), 2.02–2.16 (1H, m), 2.40–2.50 (2H, m), 3.34 (2H, dd), 3.46 (2H, dd), 4.04 (2H, dd), 4.12–4.30 (2H, m), 7.21 (1H, d), 7.57 (1H, d), 7.59 (2H, d), 7.63 (1H, dd), 7.91 (3H, d), 8.01 (1H, d), 8.55 (1H, d), 8.90 (2H, br)

EXAMPLE 18

Synthesis of (4R)-5-(1-aminoisoquinoline-7-yloxy)-4-[4-(N,N-dimethylamidino)benzoylamino]pentanoic acid bistrifluoroacetate 900 mg (1.94 mmol) of benzyl (4R)-5-(1-aminoisoquinoline-7-yloxy)-4-t-butoxycarbonylaminopentanoate was dissolved in a mixture of 5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 363 mg (1.59 mmol) of 4-(N,N-dimethylamidino)benzoic acid, 304 mg (1.59 mmol) of 1-(3-dimethylaminopropyl)-3-ethylcarbodiimide hydrochloride, 215 mg (1.59 mmol) of 1-hydroxybenzotriazole and 0.33 ml (2.39 mmol) of triethylamine were added to the obtained solution, and they were stirred at room temperature overnight. After the treatment with dichloromethane as the extraction solvent in an ordinary manner, the obtained crude product was dissolved in 10 ml of concentrated hydrochloric acid, and the obtained solution was stirred at 50° C. for one hour. The title compound was obtained in the same manner as that in step 4 in Example 1.

Yield: 340 mg (0.502 mmol) (26%)

MS (ESI, m/z) 450 (MH+)

H-NMR (DMSO-d6) δ 1.84–2.15 (2H, m), 2.33–2.44 (2H, m), 2.97 (3H, s), 3.24 (3H, s), 4.14–4.28 (2H, m), 4.36–4.52 (2H, m), 7.22 (1H, d), 7.58 (1H,d), 7.62 (1H, d), 7.70 (2H, dd), 7.91 (1H, d), 8.02 (1H, d), 8.07 (2H, dd), 8.70 (1H, d), 9.04 (2H, br), 9.38 (1H, br)

EXAMPLE 19

Synthesis of (4R)-5-(1-aminoisoquinoline-7-yloxy)-4-[4-(2-(pyridine-4-yl)ethyl)benzoylamino]pentanoic acid bistrifluoroacetate 590 mg (1.27 mmol) of benzyl (4R)-5-(1-aminoisoquinoline-7-yloxy)-4-t-butoxycarbonylaminopentanoate was dissolved in a mixture of 5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 237 mg (1.04 mmol) of 4-[2-(pyridine-4-yl)ethyl]benzoic acid, 199 mg (1.04 mmol) of 1-(3-dimethylaminopropyl)-3-ethylcarbodiimide hydrochloride, 144 mg (1.04 mmol) of 1-hydroxybenzotriazole and 0.22 ml (1.57 mmol) of triethylamine were added to the obtained solution, and they were stirred at room temperature overnight. After the treatment with dichloromethane as the extraction solvent in an ordinary manner, the obtained crude product was dissolved in 10 ml of concentrated hydrochloric acid, and the obtained solution was stirred at 50° C. for one hour. The title compound was obtained in the same manner as that in step 4 in Example 1.

Yield: 190 mg (0.267 mmol) (21%)

MS (ESI, m/z) 485 (MH+)

H-NMR (DMSO-d6) δ 1.82–1.96 (1H, m), 1.98–2.11 (1H, m), 2.12–2.29 (2H, m), 3.06 (2H, dd), 3.19 (2H, dd), 4.10–4.19 (1H, m), 4.23–4.31 (1H, m), 4.33–4.48 (1H, m), 7.20 (1H, d), 7.33 (2H, d), 7.58 (2H, d), 7.62 (1H, d),7.81 (1H, d), 7.87 (2H, d), 7.90 (1H, d), 8.08 (1H, d), 8.44 (1H, d),8.78 (2H, d), 9.06 (2H, br)

EXAMPLE 20

Synthesis of benzyl (4R)-5-(1-aminoisoquinoline-7-yloxy)-4-[(1-(4-pyridyl)-4-piperidine)carbamido]pentanoate bistrifluoroacetate 1.06 g (1.87 mmol) of benzyl (4R)-5-(1-aminoisoquinoline-7-yloxy)-4-t-butoxycarbonylaminopentanoate was dissolved in a mixture of 10 ml of 4 N solution of hydrogen chloride in dioxane and 5 ml of dioxane, and the obtained solution was stirred at room temperature for one hour. The solvent was evaporated under reduced-pressure, and the obtained crude product was dissolved in 10 ml of DMF. 386 mg (1.87 mmol) of 1-(4-pyridyl)-4-piperidinecarboxylic acid, 358 mg (1.87 mmol) of 1-(3-dimethylaminopropyl)-3-ethylcarbodiimide hydrochloride, 253 mg (1.87 mmol) of 1-hydroxybenzotriazole and 0.39 ml (2.81 mmol) of triethylamine were added to the obtained solution, and they were stirred at room temperature overnight. The title compound was obtained in the same manner as that in step 4 in Example 1.

Yield: 630 mg (0.807 mmol) (43%)

MS (ESI, m/z) 554 (MH+)

H-NMR (DMSO-d6) δ 1.48–1.66 (2H, m), 1.71–1.81 (3H, m), 1.82–2.09 (1H,m), 1.90–2.00 (1H, m), 2.53–2.65

(1H, m), 3.13–3.28 (2H, m), 4.02–4.25 (4H, m), 5.09 (2H, s), 7.19 (2H, d), 7.22 (1H, d), 7.29–7.41 (5H, m), 7.60(2H, d), 7.91 (1H, br), 7.99 (1H, d), 8.05 (1H, br), 8.22 (2H, d), 9.07 (2H, br)

EXAMPLE 21

Synthesis of (4R)-5-(1-aminoisoquinoline-7-yloxy)-4-[(1-(4-pyridyl)-4-piperidine)carbamido]pentanoic acid bistrifluoroacetate 610 mg (0.780 mmol) of benzyl (4R)-5-(1-aminoisoquinoline-7-yloxy)-4-[(1-(4-pyridyl)-4-piperidine) carbamido]pentanoate bistrifluoroacetate was dissolved in 5 ml of concentrated hydrochloric acid, and the obtained solution was stirred at 40° C. for one hour. The title compound was obtained in the same manner as that in step 4 in Example 1.

Yield: 630 mg (0.807 mmol) (43%)

MS (ESI, m/z) 554 (MH+)

H-NMR (DMSO-d6) δ 1.44–2.04 (6H, m), 2.20–2.38 (2H, m), 2.55–2.68 (1H,m), 3.08–3.30 (2H, m), 3.96–4.28 (5H, m), 7.19 (1H, d), 7.21 (2H, d), 7.58 (2H, d), 7.60 (1H, dd), 7.91 (1H, d), 8.00 (2H, d), 8.21 (2H, d), 9.00 (2H, br)

EXAMPLE 22

Synthesis of (4R)-5-(1-aminoisoquinoline-7-yloxy)-4-[4-(benzoyl)benzoylamino]pentanoic acid mono-trifluoroacetate 940 mg (1.66 mmol) of benzyl (4R)-5-(1-aminoisoquinoline-7-yloxy)-4-t-butoxycarbonylaminopentanoate was dissolved in a mixture of 5 ml of 4 N solution of hydrogen chloride in dioxane and 5 ml of dioxane, and the obtained solution was stirred at room temperature for one hour. The solvent was evaporated under reduced pressure, and the obtained crude product was dissolved in 10 ml of DMF. 375 mg (1.66 mmol) of 4-benzoylbenzoic acid, 317 mg (1.66 mmol) of 1-(3-dimethylaminopropyl)-3-ethylcarbodiimide hydrochloride, 224 mg (1.66 mmol) of 1-hydroxybenzotriazole and 0.35 ml (2.49 mmol) of triethylamine were added to the obtained solution, and they were stirred at room temperature overnight. The title compound was obtained in the same manner as that in step 4 in Example 1.

Yield: 280 mg (0.469 mmol) (28%)

MS (ESI, m/z) 484 (MH+)

H-NMR (DMSO-$d_6$) δ 1.93–2.17 (2H, m), 2.34–2.46 (2H, m), 4.16–4.30 (2H,m), 4.41–4.52 (1H, m), 7.21 (1H, d), 7.57 (2H, d), 7.60 (1H, d), 7.64 (1H, dd), 7.73 (1H, dd), 7.75 (2H, d), 7.81 (2H, d), 7.92 (1H, d), 8.02 (2H,d), 8.03 (1H, dd), 8.67 (1H, d), 8.89 (2H, br)

EXAMPLE 23

Synthesis of 3-[1-amino-(2-(4-(1-pyrrolidinecarbonyl)benzoylamino)ethoxy) isoquinoline-6-yl]-2-oxopropionic acid mono-trifluoroacetate Step 1: Synthesis of 3-hydroxy-4-iodobenzoic acid:

30.0 g (217 mmol) of 3-hydroxybenzoic acid was dissolved in 200 ml of acetic acid. 53.0 g (326 mmol) of iodine monochloride was added to the obtained solution at room temperature. They were stirred at 45° C. for 15 hours. The solvent was evaporated under reduced pressure, and the obtained residue was washed with 500 ml of 1% aqueous sodium thiosulfate solution twice and then with 500 ml of water twice, and dried to solid at 80° C. under reduced pressure to obtain the title compound.

Yield: 17.2 g (65.2 mmol) (30%)

MS (FAB, m/z) 265 (MH+)

H-NMR (DMSO-d6) δ 7.13 (1H, dd), 7.43 (1H, d), 7.80 (1H, d)

Step 2: Synthesis of methyl 4-iodo-3-methoxybenzoate:

14.9 g (56.4 mmol) of 3-hydroxy-4-iodobenzoic acid was dissolved in 200 ml of DMF. 17.5 ml (282 mmol) of methyl iodide and 39 g (282 mmol) of potassium carbonate was added to the obtained solution, and they were stirred at 50° C. for 3 hours. After the treatment with ethyl acetate as the extraction solvent in an ordinary manner, the obtained crude product was purified by the silica gel column chromatography to obtain the title compound.

Yield: 16.3 g (55.8 mmol) (99%)

H-NMR (CDCl$_3$) δ 3.90 (3H, s), 3.92 (3H, s), 7.35 (1H, dd), 7.43 (1H, d),7.84 (1H, d)

Step 3: Synthesis of 4-iodo-3-methoxybenzylalcohol:

1.5 g (5.14 mmol) of methyl 4-iodo-3-methoxybenzoate was dissolved in 20 ml of ethanol. 10 ml of 1 N sodium hydroxide solution was added to the obtained solution, and they were stirred at room temperature overnight. After the treatment with ethyl acetate as the extraction solvent in an ordinary manner, the obtained crude product was dissolved in 20 ml of THF. 1.43 ml (10.3 mmol) of triethylamine and 0.54 ml (5.65 mmol) of ethyl chloroformate were added to the obtained solution, and they were stirred for one hour. The reaction mixture was filtered to obtain the precipitate. 380 mg (10.3 mmol) of sodium borohydride was added to the precipitate under cooling with ice, and they were stirred overnight. After the treatment with ethyl acetate as the extraction solvent in an ordinary manner, the obtained crude product was purified by the silica gel column chromatography to obtain the title compound.

Yield: 930 mg (3.52 mmol) (69%)

H-NMR (CDCl$_3$) δ 3.87 (3H, s), 4.64 (2H, s), 6.67 (1H, dd), 6.85 (1H, d),7.70 (1H, d)

Step 4: Synthesis of N-(2,2-dimethoxyethyl)-N-(4-iodo-3-methoxybenzyl)-4-methylbenzenesulfonamide:

11.3 g (42.8 mmol) of 4-iodo-3-methoxybenzyl alcohol was dissolved in 250 ml of dichloromethane. 11.9 ml (85.6 mmol) of triethylamine and 7.32 g (64.2 mmol) of methanesulfonyl chloride were added to the obtained solution, and they were stirred for 2 hours. After the treatment with dichloromethane as the extraction solvent in an ordinary manner, the crude product was obtained.

13.0 g (50 mmol) of N-(2,2-dimethoxyethyl)-4-methylbenzenesulfonamide was dissolved in 150 ml of THF. 2.01 g (50 mmol) of sodium hydride was added to the obtained solution at room temperature, and they were stirred for 10 minutes. The crude product obtained as descried above was added to the resultant mixture and they were stirred for 2 hours. After the treatment with ethyl acetate as the extraction solvent in an ordinary manner, the obtained crude product was purified by the silica gel column chromatography to obtain the title compound.

Yield: 20.5 g (39.6 mmol) (92%)

H-NMR (CDCl$_3$) δ 2.42 (3H, s), 3.20 (2H, d), 3.23 (6H, s), 3.76 (3H, s),4.35 (1H, t), 4.41 (2H, s), 6.53 (1H, dd), 6.65 (1H, d), 7.28 (2H, d), 7.62 (1H, d), 7.73 (2H, d)

Step 5: Synthesis of 6-iodo-7-methoxyisoquinoline:

20.5 g (39.6 mmol) of N-(2,2-dimethoxyethyl)-N-(4-iodo-3-methoxybenzyl)-4-methylbenzenesulfonamide was dissolved in a mixture of 240 ml of dioxane and 70 ml of 6 N hydrochloric acid, and the obtained solution was heated under reflux for 2 hours. After the treatment with dichloromethane as the extraction solvent in an ordinary manner, the obtained crude product was dissolved in a mixture of 100 ml of DMF and 100 ml of t-butyl alcohol. 2.54 g (22.6 mmol) of potassium t-butoxide was added to the obtained solution and they were stirred at 40° C. for 3 hours. After the treatment with dichloromethane as the extraction solvent in an ordinary manner, the obtained crude product was purified by the silica gel column chromatography to obtain the title compound.

Yield: 7.1 g (24.9 mmol) (63%)

H-NMR (CDCl$_3$) δ 4.00 (3H, s), 7.13 (1H, s), 7.46 (1H, d), 8.32 (1H, s),8.41 (1H, d), 9.12 (1H, s)

Step 6: Synthesis of 1-chloro-6-iodo-7-methoxyisoquinoline:

7.1 g (24.9 mmol) of 6-iodo-7-methoxyisoquinoline was added to a mixture of 40 ml of acetic acid and 120 ml of 30% aqueous hydrogen peroxide solution, and they were stirred at 90° C. for 5 days. The solvent was evaporated, and the obtained residue was dissolved in 20 ml of phosphorus oxychloride. They were stirred at 100° C. for 2 hours. After the treatment with dichloromethane as the extraction solvent in an ordinary manner, the obtained crude product was purified by the silica gel column chromatography to obtain the title compound.

Yield: 2.82 g (8.86 mmol) (36%)

H-NMR (CDCl$_3$) δ 4.05 (3H, s), 7.42 (1H, d), 7.44 (1H, s), 8.16 (1H, s),8.34 (1H, s)

Step 7: Synthesis of benzyl-(6-iodo-7-methoxyisoquinoline-1-yl)amine:

2.82 g (8.86 mmol) of 1-chloro-6-iodo-7-methoxyisoquinoline was added to 15 ml of benzylamine, and they were stirred at 140° C. overnight. After the treatment with dichloromethane as the extraction solvent in an ordinary manner, the obtained crude product was purified by the silica gel column chromatography to obtain the title compound.

Yield: 2.8 g (7.18 mmol) (81%)

H-NMR (CDCl$_3$) δ 3.96 (3H, s), 4.82 (2H, d), 5.18 (1H, br), 6.85 (2H, d), 7.30–7.49 (6H, m), 7.96 (1H, d), 8.21 (1H, s)

Step 8: Synthesis of t-butyl[2-(1-amino-6-iodoisoquinoline-7-yloxy)ethyl]carbamate mono-trifluoroacetate:

2.8 g (7.18 mmol) of benzyl-(6-iodo-7-methoxyisoquinoline-1-yl)amine was dissolved in a mixture of 4 ml of acetic acid and 20 ml of hydrobromic acid, and the obtained solution was stirred at 140° C. overnight. The solvent was evaporated, and the obtained residue was dissolved in 50 ml of DMF. 2.57 g (14.4 mmol) of t-butyl (2-chloroethyl)carbamate, 4.95 g (35.9 mmol) of potassium carbonate and 2.65 g (7.18 mmol) of tetrabutylammonium iodide were added to the obtained solution, and they were stirred at 70° C. for 2 days. After the treatment with dichloromethane as the extraction solvent in an ordinary manner, the obtained crude product was treated in the same manner as that in step 4 in Example 1 to obtain the title compound.

Yield: 600 mg (1.10 mmol) (15%)

MS (ESI, m/z) 430 (MH+)

H-NMR (DMSO-d6) δ 1.39 (9H, s), 3.64 (2H, dt), 4.19 (2H, t), 7.06 (1H, d), 7.18 (1H, d), 7.60 (1H, d), 7.89 (1H, s), 8.58 (1H, s), 9.03 (2H, br)

Step 9: Synthesis of methyl 2-acetylamino-3-[1-amino-7-(2-t-butoxycarbonylaminoethoxy)isoquinoline-6-yl]acrylate mono-trifluoroacetate:

600 mg (1.10 mmol) of t-butyl [2-(1-amino-6-iodoisoquinoline-7-yloxy)ethyl]carbamate mono-trifluoroacetate was dissolved in 10 ml of DMF. 315 mg (2.20 mmol) of methyl 2-acetamidoacrylate, 234 mg (0.77 mmol) of tris(2-methylphenyl)phosphine and 0.46 ml (3.30 mmol) of triethylamine were added to the obtained solution, and they were stirred at 100° C. for 4 hours. The solvent was evaporated, and the title compound was obtained in the same manner as that in step 4 in Example 1.

Yield: 100 mg (0.18 mmol) (16%)

MS (ESI, m/z) 445 (MH+)

H-NMR (DMSO-d6) δ 1.38 (9H, s), 1.99 (3H, s), 3.40 (2H, dt), 3.74 (3H, s),4.18 (2H, t), 7.10–7.22 (2H, m), 7.24 (1H, d), 7.58 (1H, d), 7.99 (1H, s), 8.08 (1H, s), 8.92 (2H, br), 9.60 (1H, br)

Step 10: Synthesis of methyl 2-acetylamino-3-[1-amino-7-(2-(4-(1-pyrrolidinecarbonyl)benzoylamino)ethoxy)isoquinoline-6-yl]acrylate mono-trifluoroacetate:

100 mg (0.18 mmol) of methyl 2-acetylamino-3-[1-amino-7-(2-t-butoxycarbonylaminoethoxy)isoquinoline-6-yl]acrylate mono-trifluoroacetate was dissolved in a mixture of 5 ml of 4 N solution of hydrogen chloride in dioxane and 5 ml of dioxane, and the obtained solution was stirred at room temperature for 1 hour. The solvent was evaporated under reduced pressure, and the obtained crude product was dissolved in 10 ml of DMF. 40 mg (0.18 mmol) of 4-(1-pyrrolidinecarbonyl)benzoic acid, 34 mg (0.18 mmol) of 1-(3-dimethylaminopropyl)-3-ethylcarbodiimide hydrochloride, 24 mg (0.18 mmol) of 1-hydroxybenzotriazole and 0.04 ml (0.27 mmol) of triethylamine were added to the obtained solution and they were stirred at room temperature overnight. The title compound was obtained in the same manner as that in step 4 in Example 1.

Yield: 30 mg (0.046 mmol) (25%)

H-NMR (DMSO-d6) δ 1.78–1.94 (4H, m), 2.00 (3H, s), 3.28–3.55 (4H, m), 3.69 (3H, s), 3.70 (2H, dt), 4.36 (2H, t), 7.29 (1H, s), 7.55 (2H, d), 7.68(2H, d), 7.84 (2H, d), 8.04–8.15 (1H, m), 8.20 (2H, br), 8.80 (2H, br), 9.81 (1H, br)

Step 11: Synthesis of 3-[1-amino-7-(2-(4-(1-pyrrolidinecarbonyl)benzoylamino)ethoxy)isoquinoline-6-yl]-2-oxopropionic acid mono-trifluoroacetate:

30 mg (0.046 mmol) of methyl 2-acetylamino-3-[1-amino-7-(2-(4-(1-pyrrolidinecarbonyl)benzoylamino)ethoxy)isoquinoline-6-yl]acrylate mono-trifluoroacetate was dissolved in 6 N hydrochloric acid, and the obtained solution was stirred at 80° C. for 4 hours. The title compound was obtained in the same manner as that in step 4 in Example 1.

Yield: 5 mg (0.008 mmol) (18%)

MS (ESI, m/z) 491 (MH+)

H-NMR (DMSO-d6) δ 1.72–1.94 (4H, m), 3.28–3.37 (2H, m), 3.44–3.58 (2H, m), 3.66 (2H, dt), 4.36 (2H, t), 6.90 (1H, s), 7.18 (1H, d), 7.54 (1H, d), 7.58 (2H, d), 7.89 (2H, d), 8.01 (1H, d), 8.04 (1H, br), 8.81 (2H, br),

EXAMPLE 24

Synthesis of N-[2-(1-aminoisoquinoline-7-yloxy)ethyl]-4-guanidinobenzamide bistrifluoroacetate 1.0 g (3.31 mmol) of t-butyl [2-(1-aminoisoquinoline-7-yloxy)ethyl]carbamate was dissolved in a mixture of 10 ml of 4 N solution of hydrogen chloride in dioxane and 10 ml of dioxane, and the obtained solution was stirred at room temperature for one hour. The solvent was evaporated under reduced pressure, and the obtained crude product was dissolved in 10 ml of DMF. 712 mg (3.31 mmol) of 4-guanidinobenzoic acid, 632 mg (3.31 mmol) of 1-(3-dimethylaminopropyl)-3-ethylcarbodiimide hydrochloride, 447 mg (3.31 mmol) of 1-hydroxybenzotriazole and 0.92 ml (6.62 mmol) of triethylamine were added to the obtained solution, and they were stirred at room temperature overnight. The title compound was obtained in the same manner as that in step 4 in Example 1.

Yield: 230 mg (0.389 mmol) (12%)

MS (ESI, m/z) 365 (MH+)

H-NMR (DMSO-d6) δ 3.88 (2H, dt), 4.24 (2H, t), 7.22 (1H, d), 7.32 (2H, d), 7.59 (1H, d), 7.62 (1H, dd), 7.64–7.80 (4H, m), 7.91 (1H, d), 7.95 (2H, d), 8.01 (1H, d), 8.83 (1H, d), 8.97 (2H, br)

EXAMPLE 25

Synthesis of (4R)-5-(1-aminoisoquinoline-7-yloxy)-4-[4-(guanidino)benzoylamino]pentanoic acid mono-trifluoroacetate 1.0 g (2.15 mmol) of benzyl (4R)-5-(1-aminoisoquinoline-7-yloxy)-4-t-butoxycarbonylaminopentanoate was dissolved in a mixture of 10 ml of 4 N solution of hydrogen chloride in dioxane and 10 ml of dioxane, and the obtained solution was stirred at room temperature for one hour. The solvent was evaporated under reduced pressure, and the obtained crude product was dissolved in 10 ml of DMF. 462 mg (2.15 mmol) of 4-guanidinobenzoic acid, 410 mg (2.15 mmol) of 1-(3-dimethylaminopropyl)-3-ethylcarbodiimide hydrochloride, 290 mg (2.15 mmol) of 1-hydroxybenzotriazole and 0.60 ml (4.30 mmol) of triethylamine were added to the obtained solution, and they were stirred at room temperature overnight. The solvent was evaporated under reduced pressure, and the obtained crude product was dissolved in 5 ml of concentrated hydrochloric acid. The obtained solution was stirred at 50° C. for 2 hours. The solvent was evaporated under reduced pressure, and the obtained crude product was treated in the same manner as that in step 4 in Example 1 to obtain the title compound.

Yield: 100 mg (0.150 mmol) (7%)

MS (ESI, m/z) 484 (MH+)

H-NMR (DMSO-d6) δ 1.83–2.17 (2H, m), 2.30–2.43 (2H, m), 4.11–4.32 (2H, m), 4.37–4.54 (1H, m), 7.21 (1H, d), 7.32 (2H, d), 7.59 (1H, d), 7.62 (1H, dd), 7.64–7.80 (5H, m), 7.91 (1H, d), 7.95 (2H, d), 8.02 (1H, dd), 8.48 (1H, d), 9.00 (2H, br)

EXAMPLE 26

Synthesis of 3-[1-amino-7-(2-(4-(1-acetimidoyl-4-piperidyloxy)benzoylamino)ethoxy)isoquinoline-6-yl]-2-oxopropionic acid bistrifluoroacetate Step 1: Synthesis of t-butyl [2-(1-amino-6-iodoisoquinoline-7-yloxy)ethyl]carbamate:

10.4 g (26.7 mmol) of benzyl-(6-iodo-7-methoxyisoquinoline-1-yl)amine was dissolved in a mixture of 8 ml of acetic acid and 40 ml of hydrobromic acid, and the obtained solution was stirred at 140° C. overnight. The solvent was evaporated, and the residue was dissolved in 50 ml of DMF. 14.6 g (65.2 mmol) of t-butyl (2-chloroethyl)carbamate and 4.95 g (163 mmol) of potassium carbonate were added to the obtained solution, and they were stirred at 70° C. overnight. After the treatment with dichloromethane as the extraction solvent in an ordinary manner, the obtained crude product was purified by the silica gel column chromatography to obtain the title compound.

Yield: 5.6 g (13.1 mmol) (45%)

H-NMR(CDCl$_3$)δ 1.47 (9H, s), 3.62 (2H, dt), 4.21 (2H, t), 6.84 (1H, d), 7.12–7.18 (1H, m), 7.33–7.39 (1H, m), 7.60 (1H, d)

Step 2: Synthesis of methyl 2-acetylamino-3-[1-amino-7-(2-aminoethoxy)isoquinoline-6-yl]acrylate bistrifluoroacetate:

8.0 g (18.7 mmol) of t-butyl [2-(1-amino-6-iodoisoquinoline-7-yloxy)ethyl]carbamate was dissolved in 40 ml of DMF. 5.3 g (47 mmol) of methyl 2-acetamidoacrylate, 4.0 g (13 mmol) of tris(2-methylphenyl)phosphine, 7.8 ml (56 mmol) of triethylamine and 460 mg (1.87 mmol) of palladium acetate were added to the obtained solution, and they were stirred at 100° C. for 6 hours. The solvent was evaporated, and the residue was dissolved in a mixture of 20 ml of 4 N solution of hydrogen chloride in dioxane and 20 ml of dioxane. The obtained solution was stirred at room temperature for one hour. The solvent was evaporated under reduced pressure. An aqueous layer obtained by the separation with dichloromethane and 1 N hydrochloric acid was freeze-dried. The obtained crude product was treated in the same manner as that in step 4 in Example 1 to obtain the title compound.

Yield: 1.7 g (2.97 mmol) (16%)

H-NMR (DMSO-d6)δ 2.00 (3H, s), 3.34–3.41 (2H, m), 3.74 (3H, s), 4.35–4.42 (2H, m), 7.23 (1H, d), 7.26 (1H, s), 7.58 (1H, s), 8.02 (1H, s), 8.06 (1H, s), 8.18 (2H, br), 9.19 (2H, br), 9.88 (1H, br)

Step 3: Synthesis of 3-[1-amino-7-(2-(4-(1-acetimidoyl-4-piperidyloxy)benzoylamino)ethoxy)isoquinoine-6-yl]-2-oxopropionic acid bistrifluoroacetate:

947 mg (1.66 mmol) of methyl 2-acetylamino-3-[1-amino-7-(2-aminoethoxy)isoquinoline-6-yl]acrylate bistrifluoroacetate was dissolved in 10 ml of DMF. 585 mg (1.82 mmol) of 4-(1-t-butoxycarbonyl-4-piperidyloxy)benzoic acid, 342 mg (1.82 mmol) of 1-(3-dimethylaminopropyl)-3-ethylcarbodiimide hydrochloride, 245 mg (1.82 mmol) of 1-hydroxybenzotriazole and 0.69 ml (4.98 mmol) of triethylamine were added to the obtained solution, and they were stirred at room temperature overnight. The solvent was evaporated under reduced pressure, and the obtained crude product was dissolved in a mixture of 10 ml of 4 N solution of hydrogen chloride in dioxane and 10 ml of dioxane. The obtained solution was stirred at room temperature for 2 hours. The solvent was evaporated under reduced pressure, and the obtained crude product was dissolved in 10 ml of ethanol. 1.0 g (8.13 mmol) of ethyl acetimidate hydrochloride and 1 ml (6.66 mmol) of triethylamine were added to the obtained solution, and they were stirred at room temperature overnight. The solvent was evaporated under reduced pressure, and the obtained crude product was dissolved in 10 ml of 6 N hydrochloric acid. The obtained solution was stirred at 80° C. for 4 hours. The title compound was obtained in the same manner as that in step 4 in Example 1.

Yield: 340 mg (0.446 mmol) (27%)

MS (ESI, m/z) 534 (MH+)

H-NMR (DMSO-d6) δ 1.69–1.88 (2H, m), 2.00–2.16 (2H, m), 2.29 (3H, s), 3.40–3.64 (4H, m), 3.66–3.83 (2H, m), 4.26–4.39 (2H, m), 4.71–4.84 (1H, m), 6.89 (1H, s), 7.06 (2H, d), 7.16 (1H, d), 7.55 (1H, d), 7.85 (2H, d), 7.97 (1H, br), 8.61 (2H, br), 8.64 (1H, br), 8.91 (2H, br), 9.16 (1H, br)

EXAMPLE 27

Synthesis of 3-[1-amino-7-(2-(4-(1-(4-pyridyl)-4-piperidine)carbonylamino)ethoxy)isoquinoline-6-yl]-2-oxopropionic acid bistrifluoroacetate 937 mg (1.65 mmol) of methyl 2-acetylamino-3-[1-amino-7-(2-aminoethoxy)isoquinoline-6-yl]acrylate bistrifluoroacetate was dissolved in 10 ml of DMF. 474 mg (1.95 mmol) of 1-(4-pyridyl)-4-piperidinecarboxylic acid, 452 mg (2.67 mmol) of 2-chloro-1,3-dimethylimidazolinium chloride and 1.21 ml (8.06 mmol) of triethylamine were added to the obtained solution. They were stirred at room temperature overnight. The purified product was obtained in the same manner as that in step 4 in Example 1 and then dissolved in 20 ml of 6 N hydrochloric acid. The obtained solution was stirred at 80° C. for 4 hours. The title compound was obtained in the same manner as that in step 4 in Example 1.

Yield: 436 mg (0.618 mmol) (38%)

MS (ESI, m/z) 478 (MH+)

H-NMR (DMSO-d6) δ 1.52–1.70 (2H, m), 1.80–1.92 (3H, m), 2.52–2.67 (1H, m), 3.14–3.32 (2H, m), 3.49–3.62 (2H, m), 4.06–4.31 (4H, m), 6.86 (1H, s), 7.13–7.21 (3H, m), 7.54 (1H, d), 7.94 (1H, br), 8.18–8.25 (3H, m), 8.62 (1H, s), 8.93 (2H, br)

EXAMPLE 28

Synthesis of 3-[1-amino-7-(2-(4-(1-(4-pyridyl)-4-piperidine)carbonylamino)ethoxy)isoquinoline-6-yl]-acrylic acid bistrifluoroacetate Step 1: Synthesis of ethyl 3-[1-amino-7-(2-aminoethoxy)isoquinoline-6-yl]acrylate bistrifluoroacetate:

2.0 g (14.6 mmol) of t-butyl [2-(1-amino-6-iodoisoquinoline-7-yloxy)ethyl]carbamate was dissolved in 30 ml of DMF. 2.5 ml (23.3 mmol) of ethyl acrylate, 3.2 ml (23.3 mmol) of triethylamine and 65 ml (0.29 mmol) of palladium acetate were added to the obtained solution, and they were stirred at 100° C. for 4 hours. The solvent was evaporated, and the product was purified by the silica gel column chromatography and then dissolved in a mixture of 10 ml of 4 N solution of hydrogen chloride in dioxane and 10 ml of dioxane. The obtained solution was stirred at room temperature for one hour. The solvent was evaporated under reduced pressure, and the obtained crude product was treated in the same manner as that in step 4 in Example 1 to obtain the title compound.

Yield: 650 mg (1.23 mmol) (26%)

H-NMR (DMSO-d6) δ 1.28 (3H, s), 4.20–4.36 (4H, m), 4.48–4.56 (2H, m), 6.88 (1H, d), 7.16 (1H, d), 7.60 (1H, d), 8.11 (1H, d), 8.24 (1H, br), 8.33 (2H, br), 8.44 (1H, br), 9.24 (2H, br)

Step 2: Synthesis of 3-[1-amino-7-(2-(4-(1-(4-pyridyl)-4-piperidine)carbonylamino) ethoxy)isoquinoline-6-yl]-acrylic acid bistrifluoroacetate:

650 mg (1.23 mmol) of ethyl 3-[1-amino-7-(2-aminoethoxy)isoquinoline-6-yl]acrylate bistrifluoroacetate was dissolved in 5 ml of DMF. 291 mg (1.23 mmol) of 1-(4-pyridyl)-4-piperidinecarboxylic acid, 202 mg (1.23 mmol) of 2-chloro-1,3-dimethylimidazolinium chloride and 0.52 ml (3.65 mmol) of triethylamine were added to the obtained solution, and they were stirred at room temperature overnight. The solvent was evaporated under reduced pressure, and the obtained crude product was stirred at 50° C. overnight. The title compound was obtained in the same manner as that in step 4 in Example 1.

Yield: 570 mg (0.826 mmol) (67%)

MS (ESI, m/z) 462 (MH+)

H-NMR (DMSO-d6) δ 1.46–1.69 (2H, m), 1.79–1.92 (2H, m), 2.54–2.67 (1H, m), 3.10–3.22 (2H, m), 3.44–3.67 (2H, m), 4.16–4.36 (4H, m), 6.80 (1H, d), 7.17 (2H, d), 7.59 (1H, d), 7.90 (1H, d), 8.04 (1H, s), 8.21 (2H, d), 8.26 (1H, t), 8.37 (1H, s), 9.12 (2H, br)

EXAMPLE 29

Synthesis of 3-[1-amino-7-(2-(4-(1-(4-pyridyl)-4-piperidine)carbonylamino)ethoxy)isoquinoline-6-yl]-propionic acid bistrifluoroacetate [compound (i)] and methyl 3-[1-amino-7-(2-(4-(1-(4-pyridyl)-4-piperidine)carbonylamino)ethoxy)isoquinoline-6-yl]-propionate bistrifluoroacetate [compound (ii)]

570 mg (0.826 mmol) of 3-[1-amino-7-(2-(4-(1-(4-pyridyl)-4-piperidine)carbonylamino)ethoxy)isoquinoline-6-yl]-acrylic acid bistrifluoroacetate was dissolved in 5 ml of 1 N hydrochloric acid. 500 mg of Pd—C was added to the obtained solution, and they were stirred in the presence of hydrogen overnight. The title compound was obtained in the same manner as that in step 4 in Example 1.

Yield of 3-[1-amino-7-(2-(4-(1-(4-pyridyl)-4-piperidine)carbonylamino)ethoxy)isoquinoline-6-yl]-propionic acid bistrifluoroacetate: 190 mg (0.275 mmol) (33%)

MS (ESI, m/z) 464 (MH+)

H-NMR-(DMSO-d6) δ 1.51–1.68 (2H, m), 1.79–1.92 (2H, m), 2.53–2.60 (1H, m), 2.62 (2H, t), 2.99 (2H, t), 3.55 (2H, dt), 4.14–4.26 (4H, m), 7.15 (1H, d), 7.18 (2H, d), 7.56 (1H, d), 8.18–8.25 (3H, m), 8.93 (2H, br)

Yield of methyl 3-[1-amino-7-(2-(4-(1-(4-pyridyl)-4-piperidine)carbonylamino)ethoxy)isoquinoline-6-yl]-propionate bistrifluoroacetate: 100 mg (0.141 mmol) (17%)

MS (ESI, m/z) 478 (MH+)

H-NMR (DMSO-d6) δ 1.48–1.68 (2H, m), 1.80–1.92 (2H, m), 2.57–2.61 (1H, m), 2.72 (2H, t), 3.04 (2H, t), 3.17–3.28 (2H, m), 3.51–3.59 (2H, m), 3.59 (3H, s), 7.15 (1H, d), 7.19 (2H, d), 7.56 (1H, d), 7.77 (1H, s), 7.91 (1H, t), 8.17–8.26 (3H, m), 8.88 (2H, br)

EXAMPLE 30

Determination of Activity of Inhibiting the Activated Blood-Coagulation Factor X 130 μl of 100 mM tris hydrochloride buffer adjusted to pH 8.4 was added to 10 μl of an aqueous solution of a compound to be tested. Then 10 μl of a 0.5 unit/ml solution of activated human blood coagulation factor X (a product of Enzyme Research Co.) in tris hydrochloride of pH 8.4 was added to the resultant mixture. After the incubation at room temperature for 10 minutes, 50 μl of a solution of N-benzoyl-L-isoleucyl-L-glutamyl-glycyl-L-arginyl-P-nitroanilide hydrochloride (a product of Peptide Institute, Inc.) adjusted to 0.8 mM with tris hydrochloride (pH 8.4) was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC50) of a concentration of the test compound which inhibits 50% of the activity (initial rate) of the activated blood coagulation factor X in the absence of the test compound was determined, and employed as the index of the activity of inhibiting activated blood coagulation factor X. The activities, of inhibiting activated blood coagulation factor X, of representative compounds are shown in Table 1 given below.

EXAMPLE 31

Determination of Thrombin-Inhibiting Activity:

130 μl of 100 mM tris hydrochloride buffer adjusted to pH 8.4 was added to 10 μl of an aqueous solution of a test compound. Then 10 μl of a solution of human thrombin (a product of SIGMA Co.) adjusted to 2 units/ml with tris hydrochloride buffer of pH 8.4 was added to the resultant mixture. After the incubation at room temperature for 10 minutes, 50 μl of a solution of D-phenylalanyl-L-pipecolyl-L-arginyl-P-nitroanilide dihydrochloride (S-2238; a product of Daiichi Kagaku Yakuhin Co.) adjusted to 0.4 mM with tris hydrochloride buffer of pH 8.4 was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of MIO RAD) at a wave length of 405 nm at intervals of 15 seconds for 16 minutes. The negative logarithm (pIC50) of a concentration of the test compound which inhibits 50% of the activity (initial rate) of the thrombin in the absence of the test compound was determined, and employed as the index of the activity of inhibiting thrombin. The activities, of inhibiting thrombin, of representative compounds are shown in Table 1 given below.

EXAMPLE 32

Determination of Blood Anticoagulating Activity:

The blood anticoagulating activity was determined by a prothrombin time (PT) determination method. The PT was determined as follows: The blood was taken from healthy people. 3.8% aqueous trisodium citrate solution was added to the blood in a volume ratio of 1:10. The blood plasma was separated by the centrifugation. 5 μl of DMSO solution containing a test compound was added to 45 μl of the blood plasma. After the incubation at room temperature for 2 minutes, a test tube containing the blood plasma solution was placed in Sysmex CA-3000 fully automatic blood coagulation determination device (a product of To a Medical Electronics Co., Ltd.), and incubated at 37° C. for 3 minutes. 100 μl of Sysmex PT II (rabbit brain tissue thromboplastin, 13.2 mM calcium chloride; a product of To a Medical Electronics Co., Ltd.) was fed into the test tube. PT was automatically determined with the device. A sample containing 5, 1 of DMSO in place of the solution of the test compound was used as the control. The negative logarithm (PT2) of the concentration of the test compound which elongated PT of the control to the twice as long was determined, and employed as the index of the blood anticoagulating activity.

TABLE 1

|  | Activity of inhibiting activated blood coagulation factor X (pIC$_{50}$) | Thrombin-inhibiting activity (pIC$_{50}$) | Blood anticoagulating activity (PT2) |
| --- | --- | --- | --- |
| Compound of Ex. 2 | 6.6 | 3.6 | 5.5 |
| Compound of Ex. 16 | 7.1 | <3.0 | 5.6 |
| Compound of Ex. 17 | 6.6 | 3.5 | — |
| Compound of Ex. 21 | 6.8 | 3.5 | — |
| Compound of Ex. 23 | 7.6 | 4.8 | 5.6 |
| Compound of Ex. 25 | 6.4 | 3.1 | — |
| Compound of Ex. 26 | 6.7 | <3.3 | 6.2 |
| Compound of Ex. 27 | 6.6 | <3.3 | 6.2 |

It is apparent from the results that the aminoisoquinoline derivatives of the present invention have a specifically high activity of inhibiting the activated blood coagulation factor X.

The structural formulae of the compounds of the present invention synthesized in the Examples are given below.

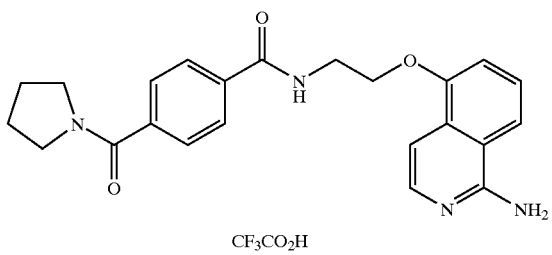

Compound of Example 1

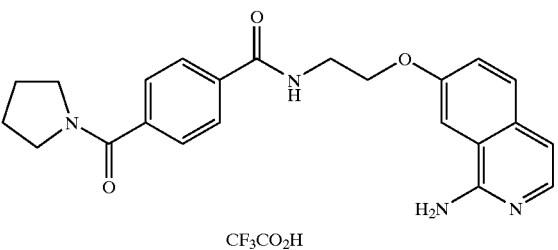

Compound of Example 2

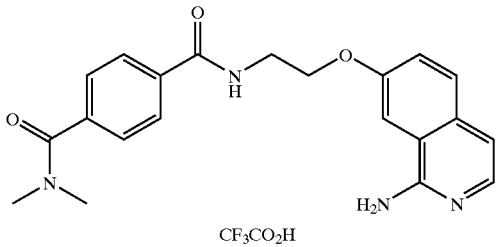

33
Compound of Example 3
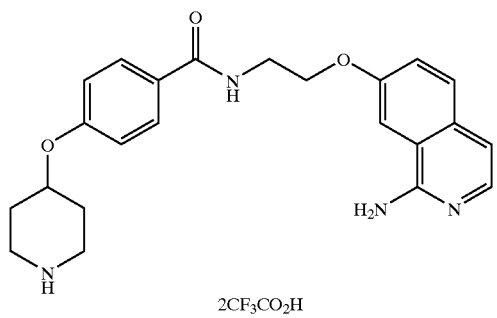
2CF₃CO₂H
Compound of Example 4
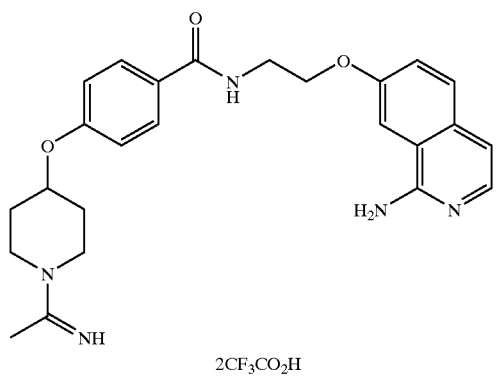
2CF₃CO₂H
Compound of Example 5
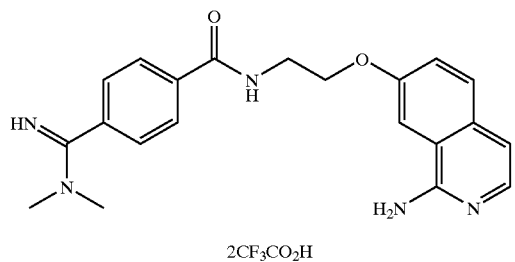
2CF₃CO₂H
Compound of Example 6
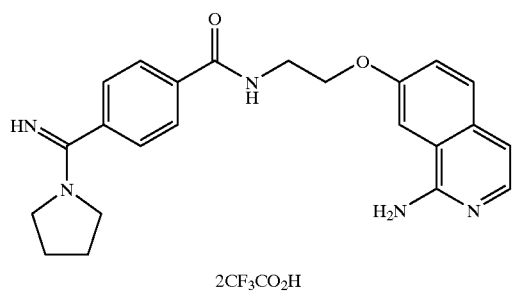
2CF₃CO₂H
34
Compound of Example 7
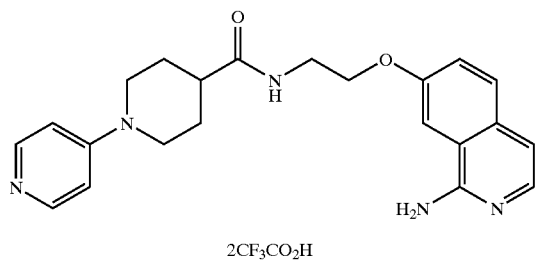
2CF₃CO₂H
Compound of Example 8
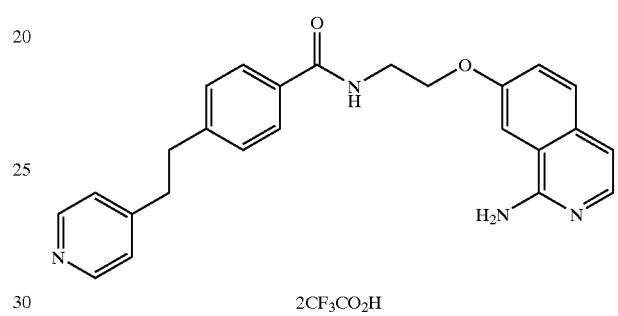
2CF₃CO₂H
Compound of Example 9
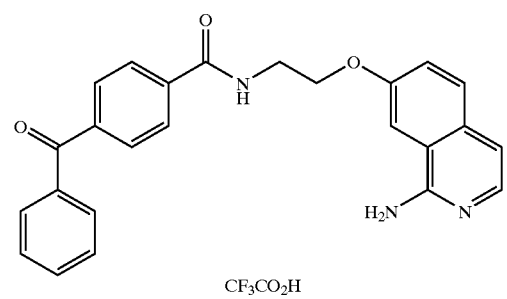
CF₃CO₂H
Compound of Example 10
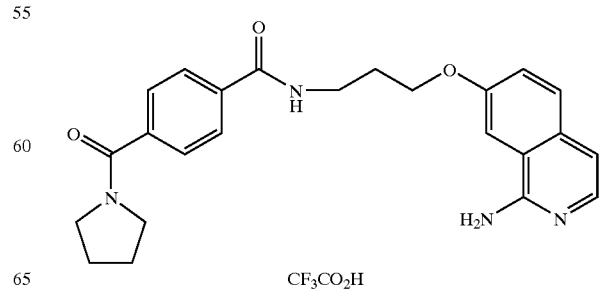
CF₃CO₂H 35
Compound of Example 11
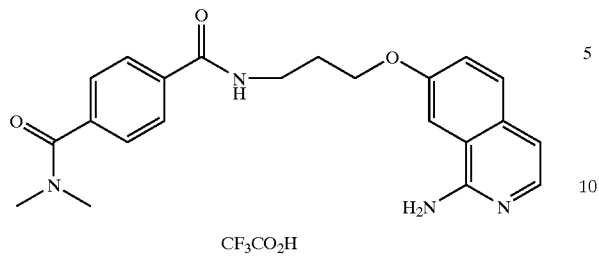
CF₃CO₂H
Compound of Example 12
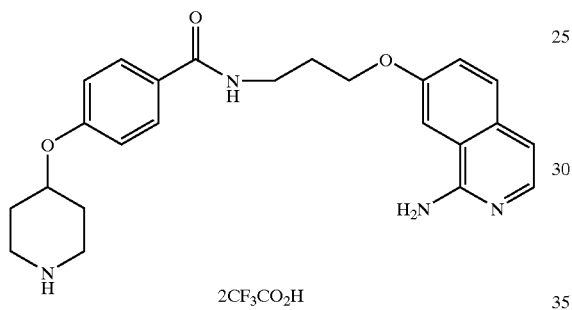
2CF₃CO₂H
Compound of Example 13
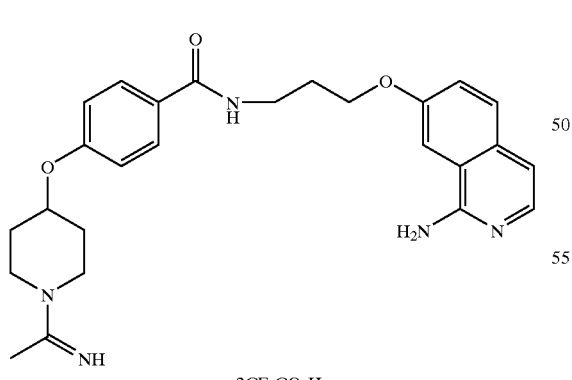
2CF₃CO₂H
36
Compound of Example 14
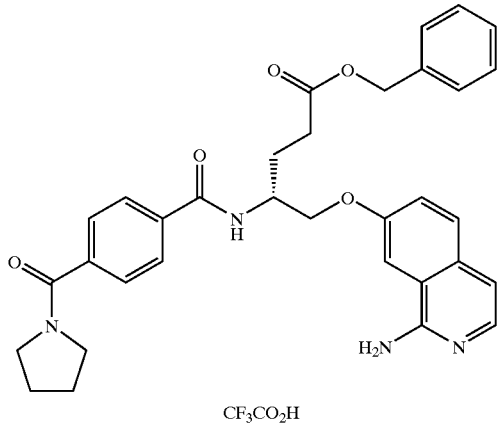
CF₃CO₂H
Compound of Example 15
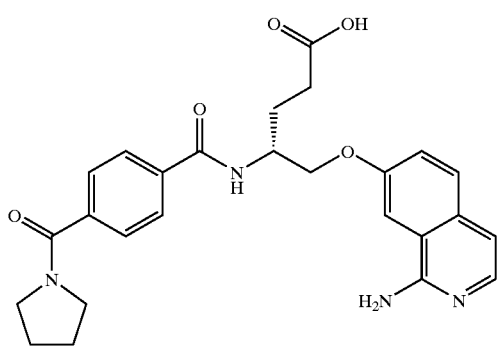
CF₃CO₂H
Compound of Example 16
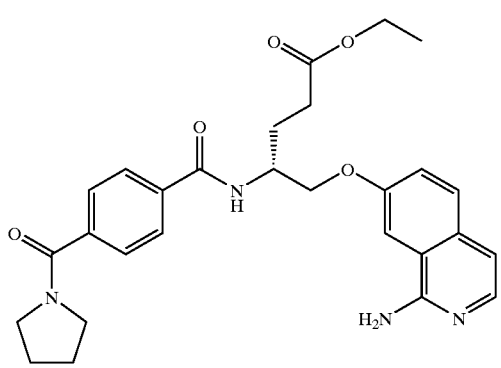
CF₃CO₂H

37
Compound of Example 17
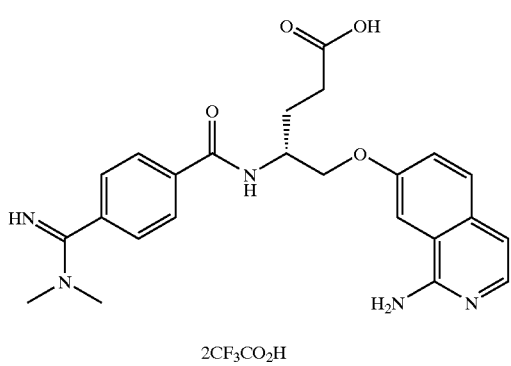
2CF₃CO₂H
Compound of Example 18
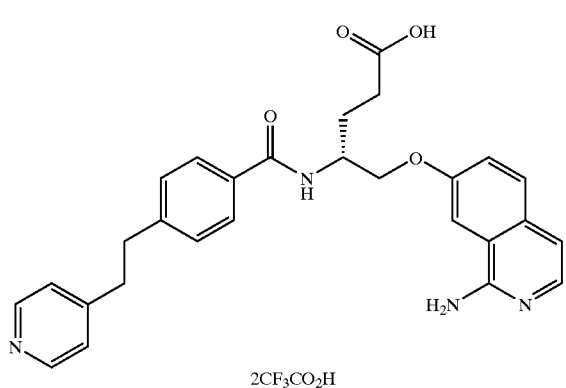
2CF₃CO₂H
Compound of Example 19
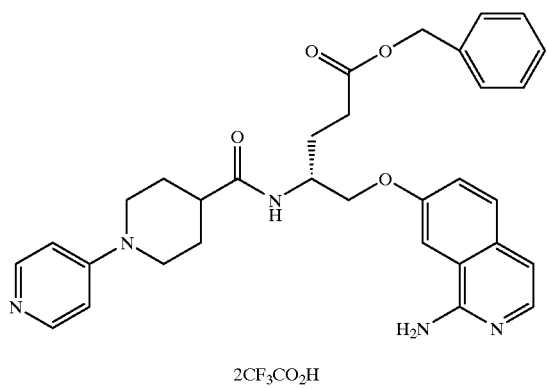
2CF₃CO₂H
38
Compound of Example 20
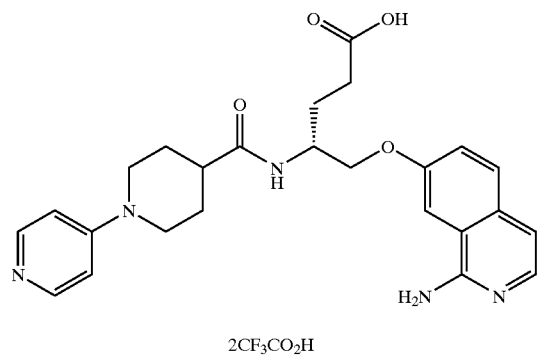
2CF₃CO₂H
Compound of Example 21
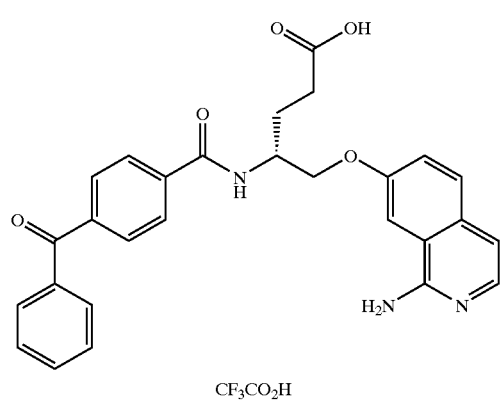
CF₃CO₂H
Compound of Example 22
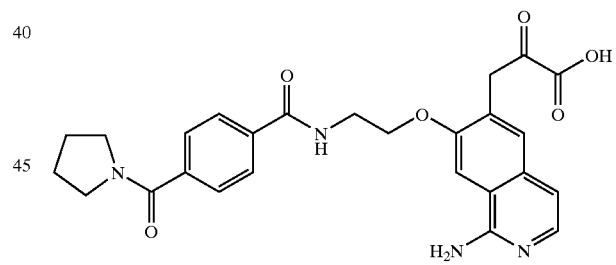
CF₃CO₂H
Compound of Example 23
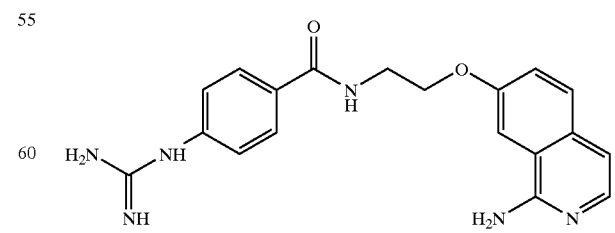
2CF₃CO₂H

39

Compound of Example 24

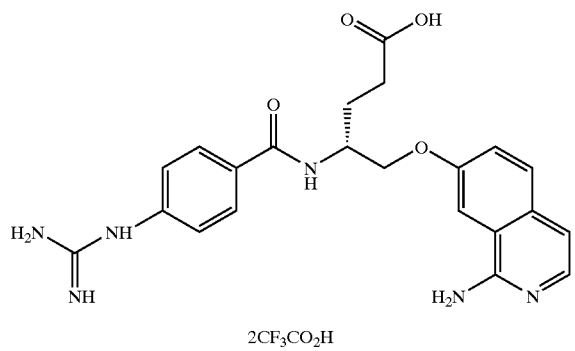

2CF₃CO₂H

Compound of Example 25

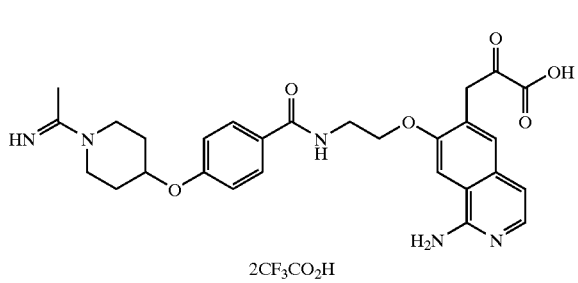

2CF₃CO₂H

Compound of Example 26

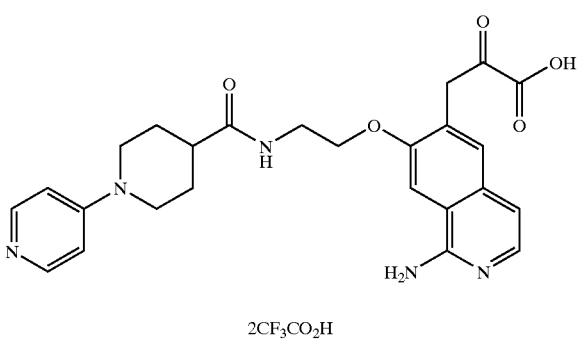

2CF₃CO₂H

Compound of Example 27

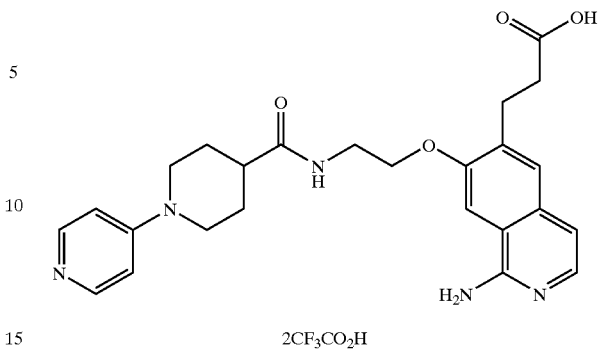

2CF₃CO₂H

40

Compound of Example 28

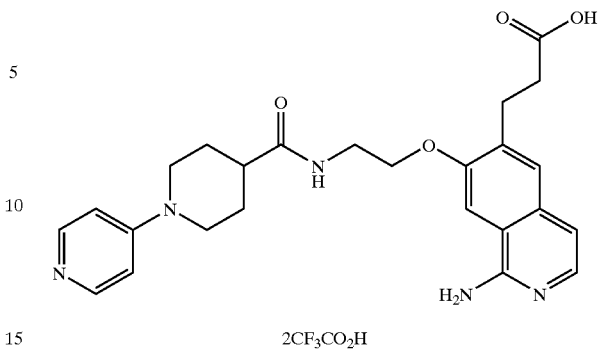

2CF₃CO₂H

Compound (i) of Example 29

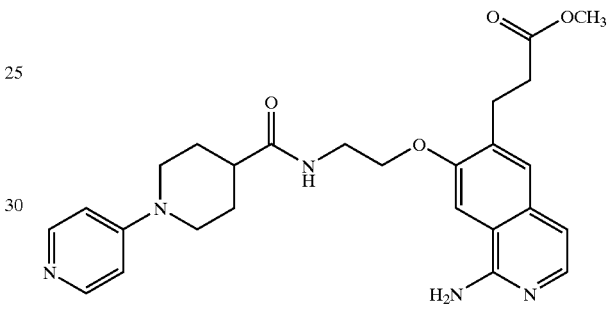

2CF₃CO₂H

Compound (ii) of Example 29

The anticoagulant containing a compound of the present invention or a salt thereof as the active ingredient has a blood-coagulation inhibiting effect based on the excellent effect of inhibiting activated blood-coagulation factor X. Therefore, the compounds of the present invention are usable as agents for preventing or treating diseases such as cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral obliteration; deep vein thrombosis; generalized intravascular coagulation syndrome; thrombus formation after an artificial blood vessel-forming operation or artificial valve substitution; re-occlusion and re-stenosis after a coronary bypass-forming operation; re-occlusion and re-stenosis after reconstructive operation for the blood circulation such as percutaneous transluminal coronary angioplasty (PTCA) or percutaneous transluminal coronary recanalization (PTCR); and thrombus formation in the course of the extracorporeal circulation.

What is claimed is:

1. An aminoisoquinoline compound of formula (1) or a pharmaceutically acceptable salt thereof:

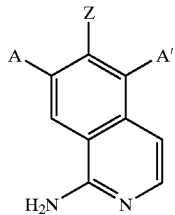
(1)

wherein A in formula (1) represents an organic group of the following formula (2) and A' represents a hydrogen atom, or A' represents an organic group of the following formula (2) and A represents a hydrogen atom:

V—L—Y— (2)

wherein L in formula (2) represents an organic group of any of the following formulae (3) to (6):

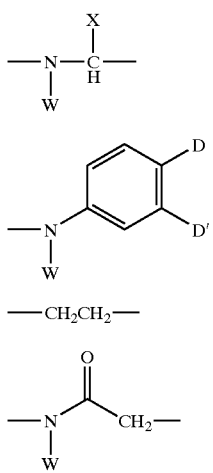
(3)
(4)
—CH$_2$CH$_2$— (5)
(6)

wherein

W in above formulae (3), (4) and (6) represents a hydrogen atom, an alkyl group having 1 to 6 carbon atoms, an aryl group having 4 to 10 carbon atoms, an aralkyl group having 5 to 12 carbon atoms or a carboxyalkylsulfonyl group having 2 to 4 carbon atoms;

one of D and D' in formula (4) represents a bond to Y in formula (2) and the other represents a hydrogen atom;

X in formula (3) represents a hydrogen atom, a carboxyl group, an alkoxycarbonyl group having 1 to 3 carbon atoms, an alkyl group having 1 to 3 carbon atoms which optionally has a substituent(s) or a benzyl group which optionally has a substituent(s), wherein the substituent(s) is selected from among carboxyl group, alkoxycarbonyl groups having 2 to 10 carbon atoms, alkylsulfonyloxy groups having 1 to 6 carbon atoms, piperidyloxy group, iminoalkylpiperidyloxy groups having 6 to 10 carbon atoms, alkoxycarbonylpiperidyloxy groups having 7 to 14 carbon atoms, piperidylalkyl groups having 6 to 8 carbon atoms, iminoalkylpiperidylalkyl groups having 7 to 11 carbon atoms, alkoxycarbonylpiperidylalkyl groups having 8 to 15 carbon atoms, pyrrolidyloxy group, iminoalkylpyrrolidyloxy groups having 5 to 9 carbon atoms, alkoxycarbonylpyrrolidyloxy groups having 7 to 13 carbon atoms, amidino group, mono- or dialkylamidino groups having 2 to 7 carbon atoms, hydroxyl group, halogeno groups, indolyl group and alkyl groups having 1 to 5 carbon atoms;

X and W in formula (3) may be bonded together to form a ring and, in this case, —W—X— represents an ethylene group, trimethylene group or tetramethylene group;

when L is an organic group of any of formulae (3) to (5), V represents a hydrogen atom, an alkanesulfonyl group having 1 to 6 carbon atoms, which optionally has a substituent(s), or a benzoyl, benzenesulfonyl, 2-naphthalenesulfonyl, cinnamoyl, piperidinecarbonyl, phenylacetyl, pyridinecarbonyl, thiophenecarbonyl, phenylthiocarbonyl or benzimidoyl group which optionally has a substituent(s);

when L is an organic group of formula (6), V represents an aryl group having 4 to 10 carbon atoms, which optionally has a substituent(s);

when L is an organic group of any of formulae (3) to (6) and V has a substituent(s), the substituent(s) is selected from among carboxyl group, alkoxycarbonyl groups having 2 to 7 carbon atoms, carbamoyl group, mono- or dialkylcarbamoyl groups having 2 to 7 carbon atoms, amidino group, mono- or dialkylamidino groups having 2 to 7 carbon atoms, trialkylamidino groups having 4 to 7 carbon atoms, acyl groups having 1 to 8 carbon atoms, halogeno groups, amino group, mono- or dialkylamino groups having 1 to 6 carbon atoms, arylamino groups having 4 to 6 carbon atoms, alkoxycarbonylamino groups having 2 to 7 carbon atoms, aminoalkyl groups having 1 to 3 carbon atoms, mono- or dialkylamino groups having 2 to 7 carbon atoms, N-alkyl-N-alkoxycarbonylaminoalkyl groups having 4 to 10 carbon atoms, piperidyloxy group, acylpiperidyloxy groups having 6 to 9 carbon atoms, iminoalkylpiperidyloxy groups having 6 to 10 carbon atoms, alkoxycarbonylpiperidyloxy groups having 8 to 14 carbon atoms, pyrrolidyloxy group, iminoalkylpyrrolidyloxy groups having 5 to 9 carbon atoms, alkoxycarbonylpyrrolidyloxy groups having 7 to 13 carbon atoms, hydroxycarbonylalkyl groups having 2 to 7 carbon atoms, alkoxycarbonylalkyl groups having 3 to 8 carbon atoms, hydroxycarbonylalkenyl groups having 3 to 7 carbon atoms, alkoxycarbonylalkenyl groups having 4 to 8 carbon atoms, aryl groups having 4 to 10 carbon atoms, arylalkenyl groups having 6 to 12 carbon atoms, alkoxyl groups having 1 to 10 carbon atoms, nitro group, trifluoromethyl group, alkyl groups having 3 to 8 carbon atoms, arylsulfonyl groups having 4 to 10 carbon atoms, arylalkyl groups having 5 to 12 carbon atoms, piperazinecarbonyl group, iminoalkylpiperazinecarbonyl groups having 7 to 10 carbon atoms, piperazinesulfonyl group, iminoalkylpiperazinesulfonyl groups having 6 to 9 carbon atoms, piperidylalkyl groups having 6 to 9 carbon atoms, iminoalkylpiperidylalkyl groups having 8 to 12 carbon atoms, piperididenealkyl groups having 6 to 9 carbon atoms, iminoalkylpiperididenealkyl groups having 6 to 9 carbon atoms, iminoalkylpiperidinealkyl groups having 8 to 12 carbon atoms, guanidino group, dialkylguanidino groups having 3 to 5 carbon atoms, phosphono group, dialkoxyphosphoryl groups having 2 to 9 carbon atoms, monoalkoxyhydroxyphosphoryl groups having 1 to 4 carbon atoms and dialkylguadinino groups having 3 to 5 carbon atoms;

Y represents a group of any of the following formulae (7) to (13):

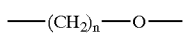 (7)

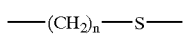 (8)

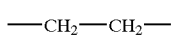 (9)

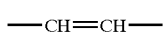 (10)

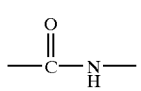 (11)

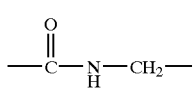 (12)

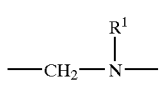 (13)

wherein n in formulae (7) and (8) represents an integer of 1 or 2, $R^1$ in formula (13) represents a hydrogen atom, a hydroxycarbonylalkyl group having 2 to 7 carbon atoms, an alkoxycarbonylalkyl group having 3 to 8 carbon atoms or a hydroxycarbonylalkenyl group having 3 to 7 carbon atoms; and Z represents a hydrogen atom, an alkyl group having 1 to 6 carbon atoms, a halogeno group, an amino group or a group of any of the following formulae (14) to (19):

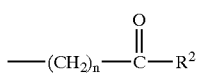 (14)

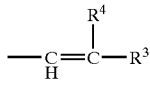 (15)

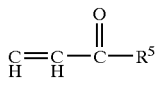 (16)

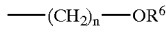 (17)

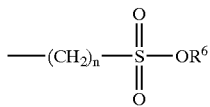 (18)

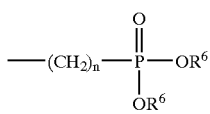 (19)

wherein n in formulae (14) and (17) to (19) represents an integer of 0 to 3, $R^2$ in formula (14) represents a hydroxyl group, a carboxyl group, an amino group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms;

$R^3$ in formula (15) represents a carboxyl group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms;

$R^4$ represents a hydrogen atom, an alkoxycarbonylamino group having 2 to 7 carbon atoms or an alkylcarbonylamino group having 2 to 7 carbon atoms;

$R^5$ in formula (16) represents a hydroxyl group, an amino group, an aryl group having 4 to 10 carbon atoms, an alkoxyl group having 1 to 3 carbon atoms or an aralkyl group having 5 to 12 carbon atoms; and $R^6$ in formulae (17) to (19) represents a hydrogen atom or an alkyl group having 1 to 6 carbon atoms.

2. The aminoisoquinoline compound or a pharmaceutically acceptable salt thereof according to claim 1, wherein Z in formula (1) represents a hydrogen atom, an alkyl group having 1 to 6 carbon atoms, a halogeno group or a group of formula (14) or (15), n in formula (14) represents an integer of 1 or 2, and $R^2$ represents a hydroxyl group, a carboxyl group, an alkoxycarbonyl group having 2 to 7 carbon atoms, an aryl group having 4 to 10 carbon atoms, an alkoxyl group having 1 to 3 carbon atoms or an aralkyl group having 5 to 12 carbon atoms.

3. The aminoisoquinoline compound or a pharmaceutically acceptable salt thereof according to claim 2, wherein when V in formula (1) has a substituent(s), the substituent(s) is selected from among 4-piperidyloxy group, 1-acetimidoyl-4-piperidyloxy group, dimethylcarbamoyl group, N,N-dimethylamidino group, 1-pyrrolidinecarbonyl group, 2-(4-pyridyl)ethyl group, 4-imino(pyrrolidine-1-yl) group, benzoyl group or 4-pyridyl group.

4. The aminoisoquinoline compound or a pharmaceutically acceptable salt thereof according to claim 2, wherein W in formula (1) is any of a hydrogen atom, methyl group or benzyl group.

5. The aminoisoquinoline compound or a pharmaceutically acceptable salt thereof according to claim 2, wherein when X in formula (1) has a substituent(s), the substituent(s) is selected from among benzyloxycarbonyl group, carboxyl group, methoxycarbonyl group, ethoxycarbonyl group, ethanesulfonyloxy group, butanesulfonyloxy group, 4-piperidyloxy group, 1-acetimidoyl-4-piperidyloxy group, 1-benzyloxycarbonyl-4-piperidyloxy group, 4-piperidylmethyl group, (1-acetimidoyl-4-piperidyl)methyl group, 1-acetimidoyl-3-pyrrolidyloxy group, isopropyl group, 3-indolyl group and iodine atom.

6. The aminoisoquinoline compound or a pharmaceutically acceptable salt thereof according to claim 2, wherein Z in formula (1) represents a hydrogen atom, iodine atom, methyl group or a 2-carboxy-2-oxoethyl group.

7. The aminoisoquinoline compound or a pharmaceutically acceptable salt thereof according to claim 2, wherein Z in formula (1) represents a hydrogen atom or a group of formula (14), wherein $R^2$ represents a hydroxyl group, a carboxyl group or an alkoxycarbonyl group having 2 to 7 carbon atoms, or a group of formula (15) wherein $R^3$ represents a hydroxyl group, a carboxyl group or an alkoxycarbonyl group having 2 to 7 carbon atoms and $R^4$ represents a hydrogen atom, A represents a group of formula (2), A' represents a hydrogen atom, V represents a benzoyl group which optionally has a substituent(s), a piperidinecarbonyl group which optionally has a substituent(s) or a pyridinecarbonyl group which optionally has a substituent(s), L represents a group of formula (3) or (5) wherein W represents a hydrogen atom or an alkyl group having 1 to 6 carbon atoms, and X represents a hydrogen atom, a carboxyalkyl group having 2 or 3 carbon atoms, and X represents a hydrogen atom, a carboxyalkyl group having 2 or 3 carbon atoms or an alkoxycarbonylalkyl group having 3 to 10 carbon atoms, and Y represents a group of formula (7).

8. The aminoisoquinoline compound or a pharmaceutically acceptable salt thereof according to claim 7, wherein Z in formula (1) represents a hydrogen atom or a group of formula (14), wherein $R^2$ represents a carboxyl group.

9. The aminoisoquinoline compound or a pharmaceutically acceptable salt thereof according to claim 7, wherein L in formula (1) represents a group of formula (3) wherein W represents a hydrogen atom, and X represents a hydrogen atom, a carboxyethyl group or an ethoxycarbonylethyl group.

10. The aminoisoquinoline compound or a pharmaceutically acceptable salt thereof according to claim 7, wherein Z in formula (1) represents a hydrogen atom or a group of formula (14), wherein $R^2$ represents a carboxyl group, and L represents a group of formula (3) wherein W represents a hydrogen atom, and X represents a hydrogen atom, a carboxyethyl group or an ethoxycarbonylethyl group.

11. An aminoisoquinoline compound of formula (20) or a pharmaceutically acceptable salt thereof:

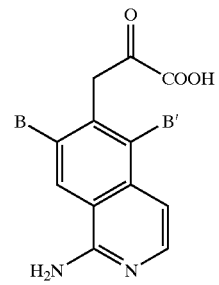

(20)

wherein one of B or B' represents an oil-soluble organic group and the other represents a hydrogen atom.

12. A medicinal composition comprising an effective amount of an aminoisoquinoline compound or a salt thereof according to claim 1 as the active ingredient and a pharmaceutically acceptable carrier or diluent.

13. A medicinal composition comprising an effective amount of an aminoisoquinoline derivative or a salt thereof according to claim 2 as the active ingredient and a pharmaceutically acceptable carrier or diluent.

14. A method for treating thrombi or emboli, comprising administering an effective amount of an aminoisoquinoline derivative or salt thereof according to claim 1 to a patient in need thereof.

15. A method for treating thrombi or emboli, comprising administering an effective amount of an aminoisoquinoline derivative or salt thereof according to claim 2 to a patient in need thereof.

* * * * *